United States Patent [19]

Funakubo et al.

[11] Patent Number: 5,106,584
[45] Date of Patent: Apr. 21, 1992

[54] CELL SELECTING APPARATUS

[75] Inventors: Hiroyasu Funakubo, Tokyo; Shinichi Miyake; Yoshikazu Nishiwaki, both of Osaka, all of Japan

[73] Assignee: Sumitomo Electric Industries, Ltd., Osaka, Japan

[21] Appl. No.: 437,287

[22] Filed: Nov. 16, 1989

Related U.S. Application Data

[63] Continuation of Ser. No. 871,426, May 15, 1986, abandoned.

[30] Foreign Application Priority Data

| Sep. 18, 1984 | [JP] | Japan | 59-195932 |
| Sep. 18, 1984 | [JP] | Japan | 59-195933 |
| Sep. 18, 1984 | [JP] | Japan | 59-195934 |
| Sep. 18, 1984 | [JP] | Japan | 59-195935 |

[51] Int. Cl.$^5$ .................. G01N 33/86; G01N 35/04
[52] U.S. Cl. .................. 422/65; 422/63; 422/67; 422/73; 436/47
[58] Field of Search .......... 422/63, 64, 65, 67, 422/73; 436/47, 63, 69; 356/39, 72, 73, 335, 336, 337, 338, 339, 340

[56] References Cited

U.S. PATENT DOCUMENTS

| 4,130,395 | 12/1978 | Chryssanthou | 422/73 X |
| 4,224,278 | 9/1980 | Hogenesch | 422/65 |
| 4,265,855 | 5/1981 | Mandle et al. | 422/65 |
| 4,318,886 | 3/1982 | Kawahara et al. | 356/39 X |
| 4,348,107 | 9/1982 | Leif | 356/72 |
| 4,362,386 | 12/1982 | Matsushita et al. | 356/39 |
| 4,643,879 | 2/1987 | Hanaway | 422/65 X |
| 4,720,463 | 1/1988 | Farber et al. | 435/291 |
| 4,727,033 | 2/1988 | Hijikata et al. | 436/69 |
| 4,812,392 | 3/1989 | Miyake et al. | 422/65 |
| 4,861,554 | 8/1989 | Sakuma | 422/67 |

FOREIGN PATENT DOCUMENTS

| 0171140 | 2/1986 | European Pat. Off. |
| 0193385 | 9/1986 | European Pat. Off. |

OTHER PUBLICATIONS

Cave et al.; An Evaluation of the Technicon H600 Haematology System; Clin. Lab. Haemat. 1983, 5, 203–214.

Primary Examiner—David L. Lacey
Assistant Examiner—Kimberly A. Trautman
Attorney, Agent, or Firm—Cushman, Darby & Cushman

[57] ABSTRACT

A cell selecting apparatus which has an extracting and injection section, a tray transport section, a cultivating section, a cell selecting section, and a controller for controlling each section according to the operating conditions which are inputted therein. This arrangement makes it possible to select and isolate the desired cells or microorganisms from mixtures of different types of cells or microorganisms, for example, those which are capable of proliferating over short periods of time and producing antibodies or secretions, from a liquid culture of cells.

8 Claims, 16 Drawing Sheets

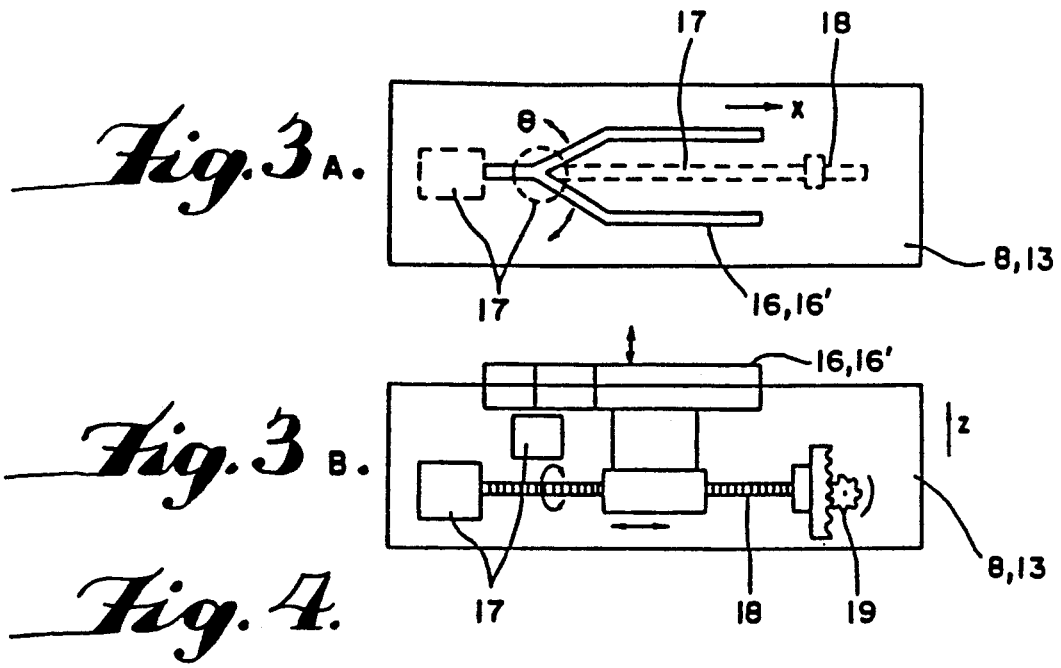
Fig. 3A.
Fig. 3B.
Fig. 4.
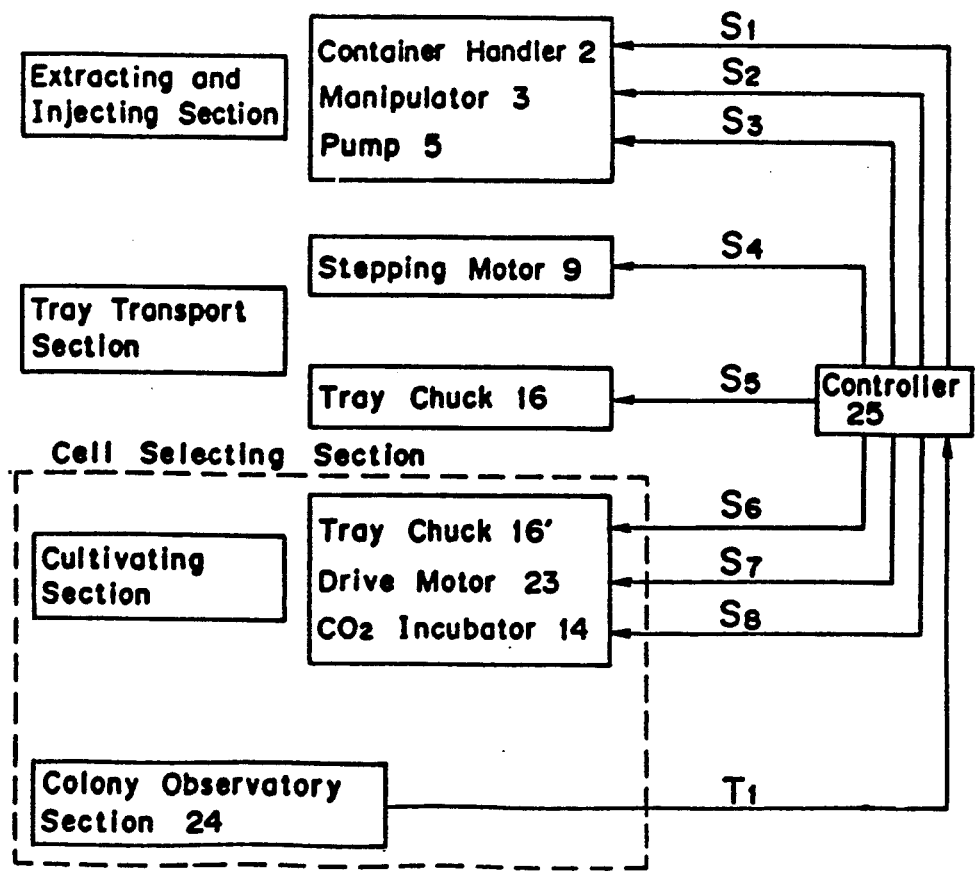

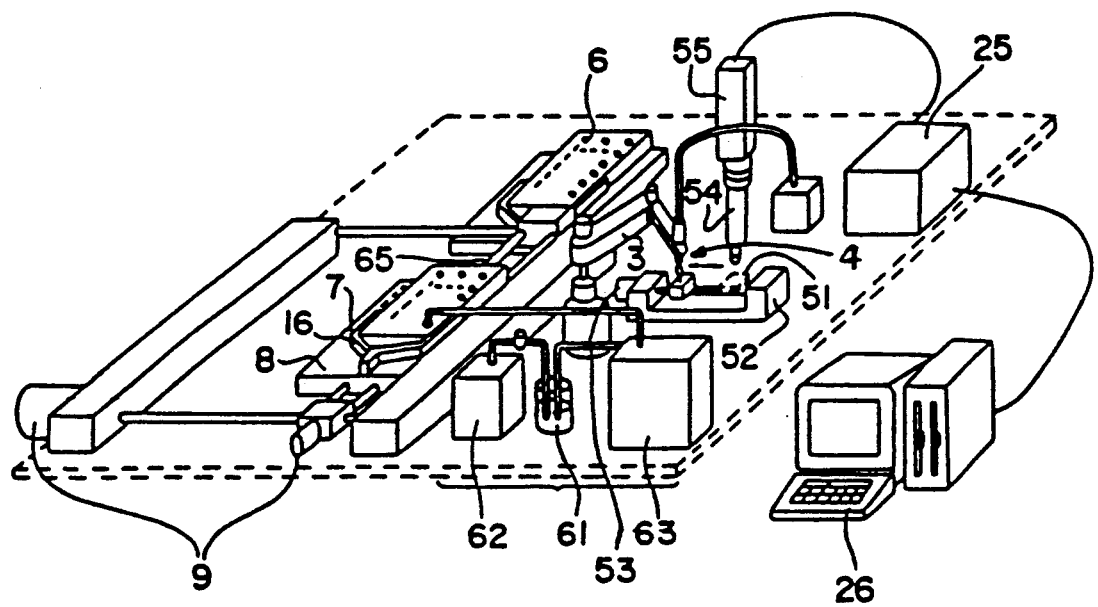

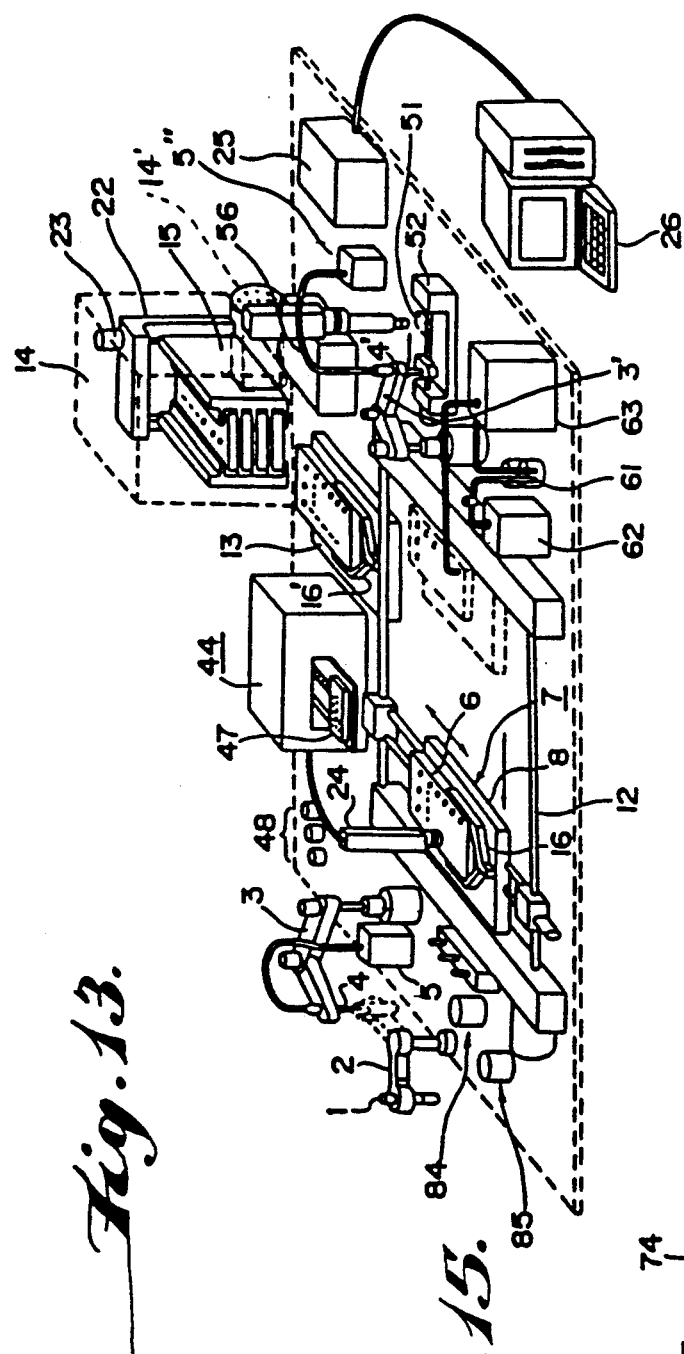
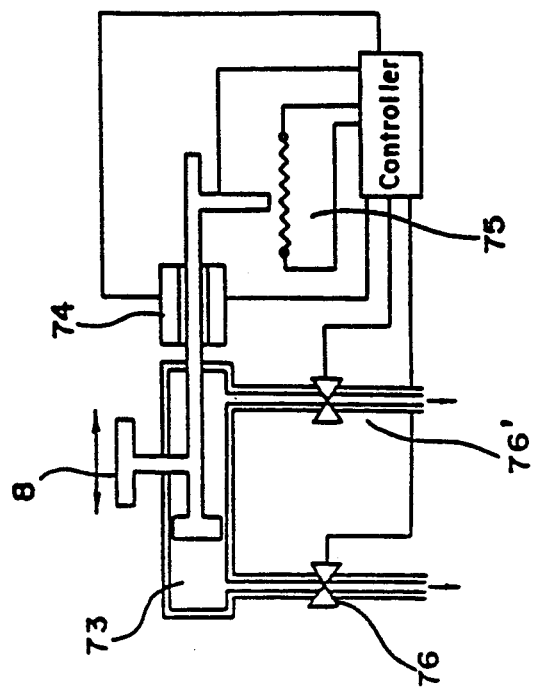
Fig. 13.
Fig. 14.
Fig. 15.

CELL SELECTING APPARATUS

This is a continuation of Ser. No. 871,426, filed May 15, 1986, now abandoned.

BACKGROUND OF THE INVENTION

1. Field of the Invention

The present invention relates to a cell selecting apparatus for selecting and isolating desired cells or microorganisms from cells or microorganisms containing different kinds of cells or microorganisms, for example, prolific cells having a high capability of producing antibodies or cells capable of producing secretions such as monoclonal antibodies from antibody producing cells capable of producing antibodies.

2. Description of the Prior Art (i) In the case where only fused cells selected from cells in which, for example, spleen cells and tumor cells are fused together are selectively proliferated by the Hypoxanthine amino protein and Thymidine (hereafter referred to as HAT) cultivation (referred to as screening), (ii) in the case where, although secretions such a monoclonal antibodies are obtained from cells capable of producing them, the monoclonal antibody producing cells are selected, (iii) in the case where cells capable of producing secretions such as antibodies are selected and isolated such as limited dilution, and (iv) in the case where the monoclonal antibody producing cells are selected and produced, the following respective methods have hitherto been employed.

Case (i)

Spleen cells ($2.5 \times 10^8$ in number) and tumor cells ($2.5 \times 10^7$ in number) are fused together by the use of polyethylene glycol as a fusion accelerator and, after centrifugation, a fusion liquid is discarded, followed by the addition of a liquid HAT culture (a liquid culture containing Hypoxanthine, Aminopfterin and Thymidine) to disperse the cells. Thereafter, the cell containing liquid obtained by dispersion are distributed in, for example, 0.2 ml into each well provided in a tray, which is in turn cultivated for two weeks in a $CO_2$ incubator. By this cultivation, the non-fused cells can be killed and the fused cells can be proliferated. Whether or not the fused cells have been proliferated can be determined by observing the presence or absence of colonies.

Case (ii)

In continuance to case (i), and with respect to the wells in which the fused cells have been determined as proliferated, the supernatant of the liquid cultures thereof is extracted by the use of micropipette and is then injected in each well of a tray for the detection of antibodies. The tray for the detection of the antibodies having the wells filled with the liquid culture supernatant is loaded in an antibody detecting section to measure the quantity of the antibodies contained in the supernatant. This measurement is usually carried out by means of ELISA (Enzyne linked immuno sorbent assay) and with it the quantity of the antibodies produced by the cells contained in the wells can be revealed. At this time, while the number of wells into which the cell liquid has been injected was, for example 480, it will be found that about 5 wells will show the production of the desired antibodies.

Case (iii)

In continuance to case (i), the liquid culture supernatant in the wells which according to the observation of the colonies have been deemed as containing the fused cells that had been proliferated is extracted and injected and is detected by means of ELISA as to whether or not the culture supernatant contains the desired antibodies. Subsequently, the cell fluid producing the desired antibodies is added with a diluting liquid in a quantity enough to permit the number to be counted by the use of a microscope, thereby to disperse the cells uniformly, and thereafter, the number of the fused cells is counted. This measurement is carried out by counting the number of cells with a microscope observation and calculating the total number of cells contained in the cell fluid.

Subsequently, the cell fluid is diluted so that, from the number of the cells obtained, one can be injected into three wells. This is for the purpose of increasing the probability that, to make it a monoclone, two or more cells will not be injected into each well. After thymocytes having no capability of producing antibody have been added so that the cells diluted and injected can proliferate, the probability of being monoclone is increased by repeating a process of dilution-injection-cultivation and monoclonal antibody producing cells are isolated.

Case (iv)

In continuance to case (iii) and in order for the cells to be subsequently proliferated, a certain number is required and therefore the thymocytes having no capability of producing antibody are added.

By repeating the above process two times (the process from the dispersion of the cells by the addition of HAT culture to the addition of the thymocytes subsequent to the injection of the cell fluid into the wells, this process is referred to as a limited dilution), the probability of being the monoclone is increased, the monoclonal antibody producing cells so obtained are proliferated to a greater number, and a greater number of monoclonal antibodies is produced.

The monoclonal antibody so obtained is utilized in research in antibody chemistry and antigen chemistry to analyze the molecular structure and genes or their function, research in pharmacology into hormones and receptors of neuron mediators, and in other studies of virus, parasites and bacterium. In addition, the use is made in the molecular biochemical assay of immune deficiency syndrome and the detection of antigens (malignant tumor, etc.) so far as the diagnosis is concerned, and also, so far as the therapeutic treatment is concerned, the use is made to the organ transplantation (organ competency), the passive immunity (injection of antibody), and the treatment of malignant tumor.

As hereinabove described, the monoclonal antibody finds large fields of applications. However, hitherto, as hereinabove described, the selection of desired cells or microorganisms resistant to the liquid culture of certain composition, for example, monoclonal antibody producing cells, from cells or microorganisms containing different kinds of cells or microorganisms is carried out manually, but there are problems in that the probability that the desired monoclonal antibody producing cells can be obtained is low, in that the cells so obtained are highly unstable (that is, easy to be killed), and in that there is a great possibility that various germs may mix up during the selecting job, and therefore, when it comes to the selection of the cells capable of producing a great number of highly active monoclonal antibodies, the selection is required to start from a huge number of fused cells. Thus, in either case, increased manual labor and increased time are required.

Furthermore, this type of selection requires a high level of technique, and in order to acquire this technique, a training period of normally 1 to 2 years is required and, therefore, the number of technicians qualified to perform the selection of the monoclonal antibody producing cells is very small. Because of it, the number of cells handled during a series of experiments is limited, and accordingly, the probability of the desired monoclonal antibody producing cells being obtained is low and even if they are obtained the capability of producing the antibody is low. In this way, they constitute an obstruction to the application of monoclonal antibodies.

OBJECT OF THE INVENTION

The present invention has for its object to minimize the manual intervention during the selection of the cell, thereby to minimize the possibility of the various germs being mixed during the selection job and to facilitate the efficient and stable selection of the cells.

In order to accomplish this object, the present invention provides a cell selecting apparatus comprising an extracting and injecting section, a tray transport section, a controller and a cell selecting section, which is characterized in that said extracting and injecting section comprises a pipette, a manipulator for holding the pipette, and a pump for sucking and discharging a predetermined quantity of liquid into and from said pipette, said tray transport section comprises a tray support for the support thereon of said tray and a drive means for transporting said tray support to predetermined positions of said extracting and injecting section and said cell selecting section, and said controller is a device for controlling each said section according to operating conditions for each said section which are inputted thereto.

If the present invention is shown in block diagram, it will be such as shown in FIG. 1. The present invention makes use of the extracting and injecting section A, the tray transport section B, the controller D and the cell selecting section C, the controller D being employed in the form of a computer in which work conditions for each of the sections are normally programmed.

From the controller D to the extracting and injecting section A, control signals $S_1$ and $S_2$ for instructing respective operations of the manipulator and the pump constituting the extracting and injecting section are generated. The control signal $S_1$ is indicative of, for example, the manipulator and the sequence and direction of operation. The control signal $S_2$ is indicative of the quantity to be sucked or discharged at the extracting and injecting section and the timing of suction or discharge.

From the controller D to the tray transport section B, signals $S_3$ and $S_4$ for instructing the operation of each of a stepping motor and a tray chuck constituting the tray transport section B (for example, the position for the transport of the tray support, the sequence of transport, the operating procedure of the tray chuck at the tray transport section, etc.) are generated.

From the controller D to the cell selecting section C, a plurality of control signals $S_5$ to $S_n$ according to the construction of the cell selecting section are generated, and from the cell selecting section C to the controller D, measurement signals $T_1$ to $T_n$ for controlling operating signals to the other sections are generated.

In the present invention, the cell selecting section comprises a cultivating section and a colony observatory section where only fused cells out of the cells wherein spleen cells and tumor cells are fused together are selectively proliferated by HAT culture, that is, where the screening is effected.

Where antibodies of the fused cells are detected and the quantity of the antibodies produced is desired to be determined, the cell selecting section in the present invention comprises an assay section, and where it is applicable to the well from which colonies can be observed and the presence or absence of colonies resulting from the proliferation of the fused cells is desired to be observed before the detection of the antibodies, the cells selecting section may comprise a colony observatory section in addition to the assay section.

Where the cells are individually isolated and distributed into wells, the cell selecting section in the present invention may comprise a cell number counting section and a cell isolating section. In the case of the cultivation of a great number of monoclonal antibody cells to be produced so that monoclonal antibodies can be produced, the cell selecting section in the present invention may comprise a cultivating section, an assay section and a cell isolating section.

According to the present invention, the selection of cells can readily be carried out with no special high technique required, merely by setting conditions for each of the sections and then starting the apparatus and, therefore, the required labor can be considerably reduced. Also, since the possibility of the various germs being mixed is eliminated and the handling capacity can be increased, the selection of the desired cells such as monoclonal antibody producing cells can be efficiently performed constantly at all times.

Furthermore, while two to three months have hitherto been required to obtain a single monoclonal antibody producing cell, the apparatus of the present invention makes it possible to complete in about one month to the proliferation of the monoclonal antibody producing cells and, during this period, different kinds of monoclones can be continuously handled simultaneously.

BRIEF DESCRIPTION OF THE DRAWINGS

The present invention will now be described in detail with reference to the drawings.

FIG. 3 is a top plan view (A) and a side view (B) of a tray support at a tray transport section or a cultivating section.

FIG. 4 is a block diagram of the first embodiment.

FIG. 9 is a perspective view of a third embodiment wherein the cell selecting section is comprised of a cell number counting section and a cell isolating section.

FIG. 10 is a sectional view of a cell isolating and injecting section.

FIG. 13 is a perspective view of a fourth embodiment wherein the cell selecting section is comprised of a cultivating section, a colony observatory section, an assay section and a cell isolating section.

FIG. 14 is a schematic diagram showing an example of driven means of the tray transport section.

FIG. 15 is a schematic diagram showing another example of the drive means of the tray transport section.

DETAILED DESCRIPTION OF THE PREFERRED EMBODIMENTS

The best mode for carrying out the present invention will be described in connection with the embodiments.

EMBODIMENT 1

The embodiment wherein the cell selecting section in the present invention comprised of a cultivating section and a colony observatory section will now be described with reference to the FIG. 2.

Figure 1:
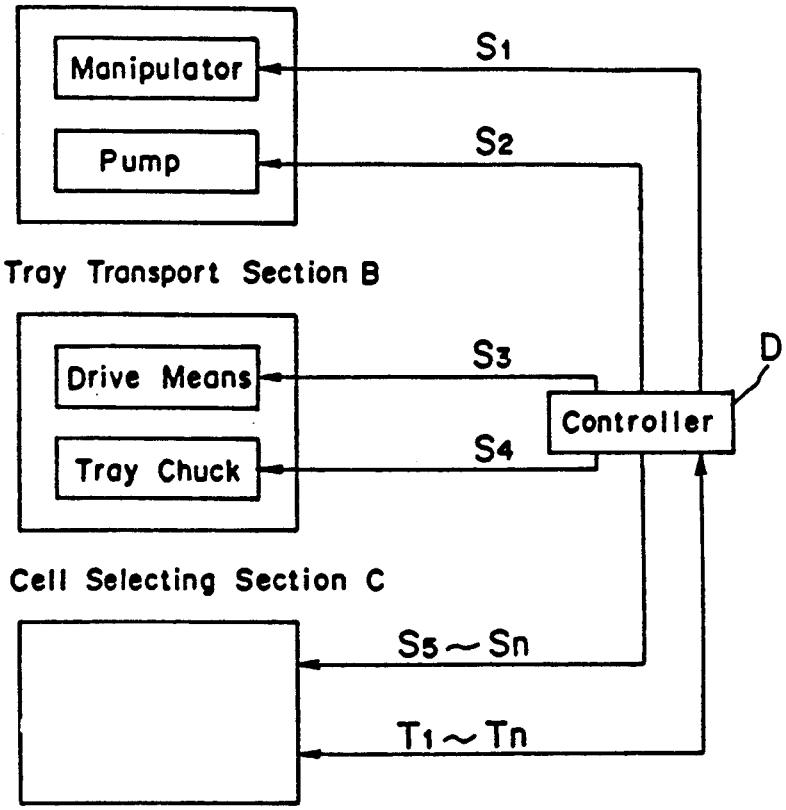
FIG. 1 is a block diagram showing the flow of signals in the cell selecting apparatus according to the present invention.
Figure 2:
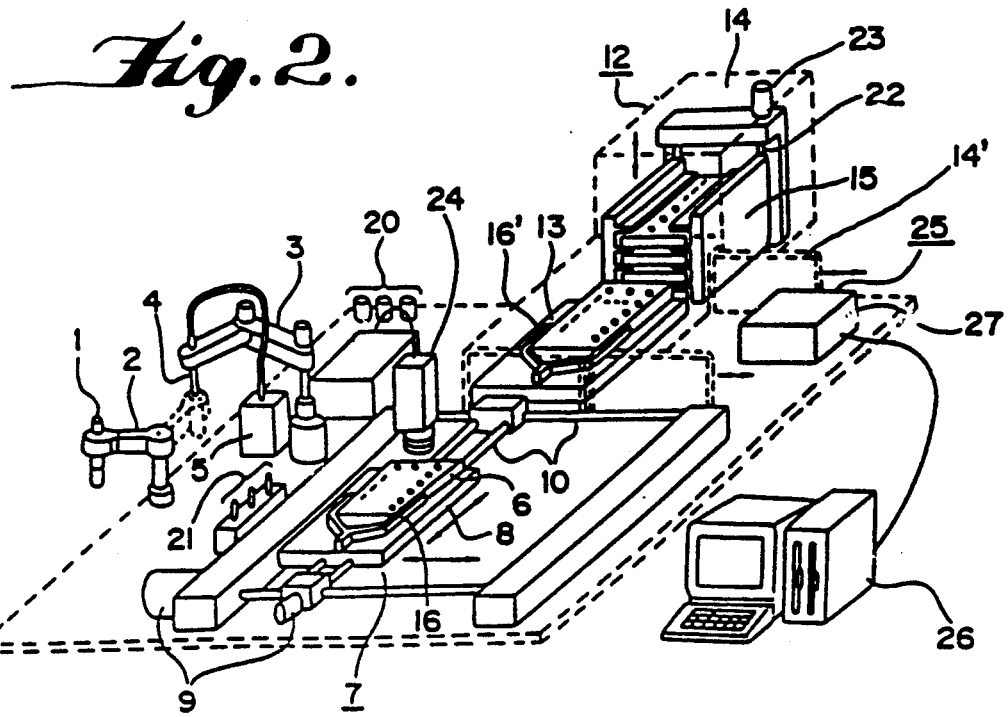
FIG. 2 is a perspective view showing an embodiment (first embodiment) wherein the cell selecting section is comprised of a cultivating section and a colony observatory section.
Figure 5:
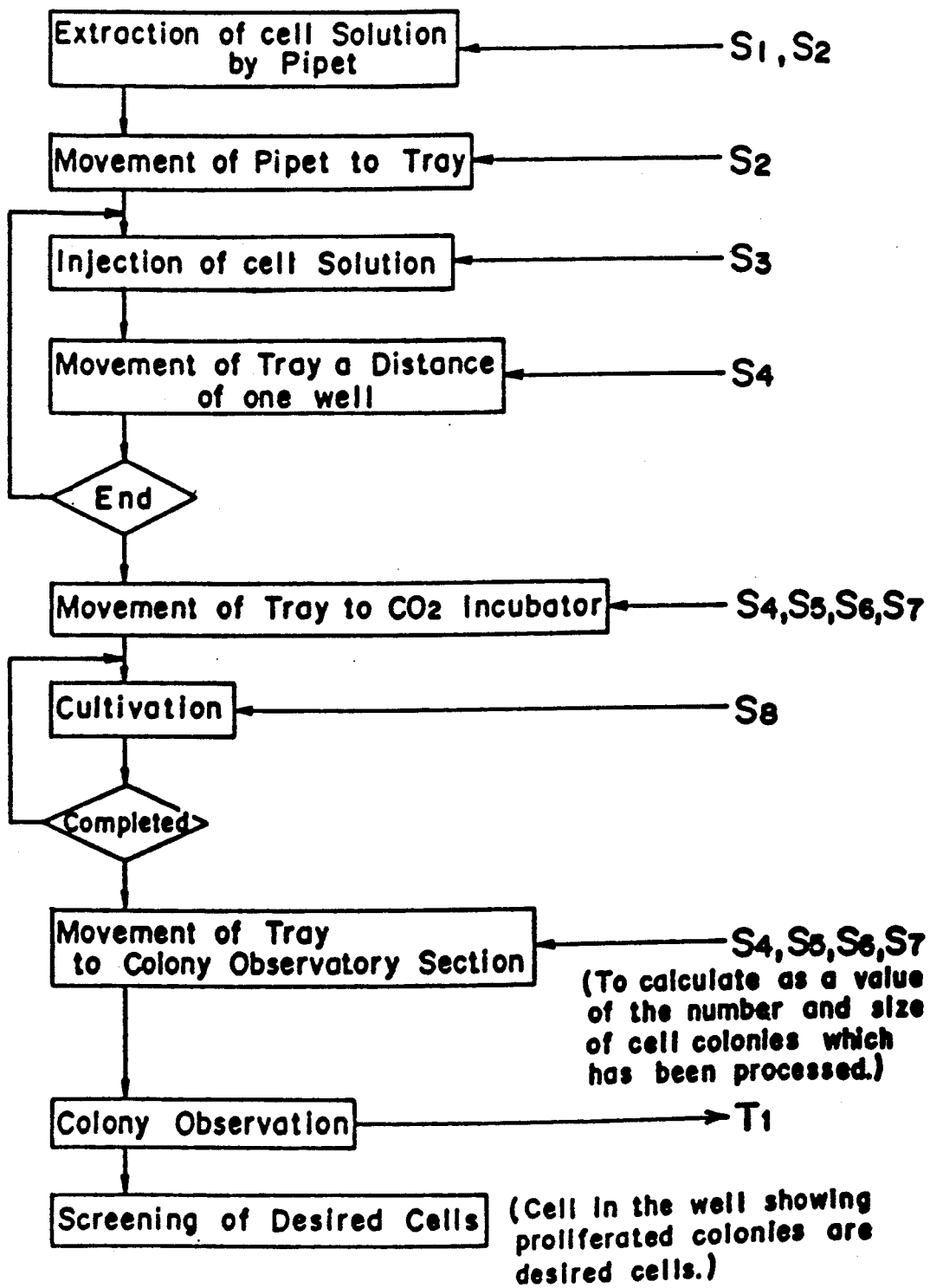
FIG. 5 is a flow diagram of the operation of the first embodiment.

A screening device shown in FIG. 2 is a device comprising an extracting and injecting section, a tray transport section, a cultivating section, a colony observatory section and a controller, wherein the extracting and injecting section comprises a pipette 4, a manipulator 3 for holding said pipette 4 and a pump 5 for sucking and discharging a predetermined quantity of liquid into and from said pipette 4, the tray transport section 7 comprises a transport section tray support 8 for the support thereon of a tray 6 having a plurality of wells provided therein, and drive means 9 and 10 for transporting said tray support 8 to respective predetermined positions of said extracting and injecting section, the cultivating section 12 and the colony observatory section, the cultivating section 12 comprises an incubator 14 equipped with a tray stop for accommodating a plurality of trays 6 and drive means for moving the tray stock, and a cultivating section tray support 13 for transporting said tray 6 to said tray stock, and the controller is a device for controlling each said section as shown in FIGS. 4 and 5 according to operating conditions for each said section inputted thereto.

A container 1, such as a tube, containing a liquid culture and cells or microorganisms is grasped by a container handler 2 and the tube is moved to a location of the manipulator 3. The container handler 2 has its tip fitted with an air-driven or motor-driven chuck with which the tube is grasped. When the manipulator 3 is operated, the pipette 4 grasped by said manipulator 3 is inserted into the tube and the solution is sucked by the pump 5.

It is to be noted that, in the present invention, the container or the like may be directly placed, without the container handler, at the place where the pipette 4 is inserted.

The manipulator 3 causes the pipette 4 to move a position above the wells of the tray 6, and a predetermined quantity of the solution is discharged into the wells by means of the pump 5.

By the movement of the tray transport section 7 or the movement of the manipulator 3, the pipette 4 is moved to above the different well and, similarly, a predetermined quantity of the solution is discharged into the well. By repeating this operation, the solution is injected into each of the wells. The pipette manipulator 3 may employ an arm of horizontally articulated type, an arm of transverse type, etc. The pump 5 controls the quantity of discharge according to the value of pressure and the time of application of the pressure. The tray transport section 7 is constituted by the transport section tray support 8 for the support of the tray 6 and drive means, for example, a stepping motor 9 and a feed screw (ball screw) 10, for transporting the transport section tray support to the predetermined positions of said extracting and injecting section, the cultivating section and the colony observatory section, the positioning of the tray being carried out according to the number of input pulses fed to the stepping motor 9. As the drive means, other than it, it may be such as operated by a wire drive or an air drive. The tray 6 having the wells fitted with the solution is grasped and fixed by the chuck 16 provided in the transport section tray support 8 and, after the injection, the tray 6 is subsequently transported by the movement of the transport section tray support 8 to a position frontwardly of the cultivating section tray support 13 provided in the cultivating section 12. Where the injection is carried out at a predetermined position of the cultivating section 12 (for example, adjacent to and frontwardly of the cultivating section tray support 13), the movement of the transport section tray support 8 may not be performed.

The tray 6 to which the solution has been injected is accommodated from the transport section tray support 8 to the cultivating section tray support 13 and into the tray stock 15 within the $CO_2$ incubator 14 constituting the cultivating section 12. The sequence of operation of said tray 6 will be hereinafter described.

As shown in FIG. 3, the transport section tray support 8 and the cultivating section tray support 13 are provided with respective tray chucks 16 and 16'. Said tray chucks 16 and 16' can be driven by a motor drive or an air drive to perform a closing and opening operation in a $\theta$ direction and the movement in x and z directions. It is to be noted that, in FIG. 3, (A) is a plan view of the tray support and (B) is a side view, 17 is a motor, 18 is a ball screw and 19 is a rack and pinion.

The tray 6 grasped and fixed by the tray chuck 16 of the transport section tray support 8 and having the solution injected into each well moves the tray chuck 16 in the x direction and transports onto the cultivating section tray support 13. At this time, the tray chuck 16' of the cultivating section tray support 13 is positioned beneath an upper surface of said tray 13. When the tray 6 is brought to a predetermined position above the cultivating section tray support 13, the tray chuck 16' moves in the z direction, grasps the tray 6, further moves in the x direction and inserts into the tray stock 15.

In FIG. 2, after the passage of a predetermined period within the $CO_2$ incubator 14, the tray 6 is moved out from the tray stock 15 within the $CO_2$ incubator 14 and then onto the transport section tray support 8 by the reverse operation.

Subsequently, with the pipette provided to the manipulator 3, culture supernatant in each well is partially sucked and discarded, and a predetermined quantity of new liquid culture 20 is injected by the use of the pipette manipulator 3 and the pump 5. At this time, in order to avoid any contamination between the liquid cultures in the wells and between the liquid culture in the well and the new liquid culture, the tip of the pipette 4 is replaced with a spare pipette tip 21. A tip fitting portion of the pipette 4 forms a motor-driven or air-driven chuck (not shown), and the pipette tip can be fitted and removed by closing and opening it.

In this way, the tray 6 added with the new liquid culture 20 is again accommodated in the tray stock 15 in the $CO_2$ incubator 14 by the tray transport section 7 and the cultivation is continued. It is to be noted that, in FIG. 2, the tray stock 15 at the cultivating section 12 is moved up and down or left and right by a drive means to accommodate a plurality of trays 6 successively. The drive means for the tray stock 15 comprises, as shown in FIG. 2, for example, a feed screw 22 and a drive motor 23.

The tray 6 after the cultivation is, by the reverse operation, transported from the cultivating section 12 to the transport section tray support 8 of the tray transport section 7 and is further transported so as to permit the wells of the tray 6 to be positioned beneath the colony observatory section 24. Each well is inspected by, for example, a TV camera constituting the colony observatory section 24, and by calculating the number and size of the colonies, the degree of proliferation is determined. Alternatively, the degree of proliferation may be determined by measuring the intensity of light transmitted through the solution.

It is to be noted that the above described $CO_2$ incubator as well as said component parts can be operated in a sterile environment while covered by an outer covering so as to permit sterile air to be flowed therethrough.

The controller 25 is a device comprised of an input device 26 and a control section 27 and is controlled by the control section according to operating conditions for each said section inputted by the input device 26 (the quantity to be sucked and discharged, the sequence of operation of the manipulator, etc., at the extracting and injecting section, the transport position of the transport section tray support, the sequence of transport, the operation of the tray chuck, etc. at the tray transport section, cultivation conditions (temperature, time, $CO_2$ quantity, etc.), the movement of the tray stock, the operation of the cultivating section tray support, etc. at the cultivating section, and the counting, etc., at the colony observatory section) and operating conditions among the sections.

A block diagram and an operation flow diagram of Embodiment 1 are respectively shown in FIGS. 4 and 5. A control signal $S_6$ is, for example, a tray chuck opening and closing signal, and $S_8$ is a signal indicative of, for example, a predetermined temperature, the $CO_2$ quantity (closure and opening of a valve), and the humidity (supplement of water of a water tray in the incubator and closure and opening of a vapor valve).

A control signal $S_1$ generated from the controller is a signal used to control the closure and opening of the chuck of the container handler, and the rotation and the lifting and lowering of the container handler, and the control signal $S_2$ is a signal used to control a drive motor in the manipulator.

In response to the signals $S_1$ and $S_2$, the container handler 1 and the manipulator 3 are operated and a cell solution is extracted by the pipette 4 from the container 1.

Subsequently, the manipulator 3 is operated in response to signal $S_2$ to move the pipette 1 to a position above one of a plurality of wells provided on the tray 6.

The pump 5 is operated in response to the control signal $S_3$ to inject the cell solution in the pipette 4 into the well.

Then, the stepping motor 9 of the tray transport section 7 is operated in response to a control signal $S_4$ to move the tray 6 a distance corresponding to one well of the tray 6 and to repeat the above described operation of the manipulator 3.

After the completion of injection of the cell solution into all of the wells on the tray 6, the control signal $S_4$, a control signal $S_5$ for controlling the operation of the tray chuck 16 (the closure and opening in the $\theta$ direction and the movement in the x and y directions shown in FIG. 3) at the tray transport section, a control signal $S_6$ for controlling the operation of the tray chuck 16' at the cultivating section, and a control signal $S_7$ for controlling the operation of a drive motor in the incubator 14 are generated from the controller 25 to the respective section, and the tray 6 is moved to the $CO_2$ incubator and accommodated in the tray stock 15.

At the cultivating section, predetermined cultivating conditions are maintained by a control signal $S_4$ indicative of the closure and opening of a door of the $CO_2$ incubator 14, the cultivation temperature, the cultivation time, the $CO_2$ quantity (the closure and opening of a valve disposed on a $CO_2$ supply pipe) and the humidity (supplemental of water of the water tray provided in the incubator, the closure and opening of the vapor valve, etc.).

After the completion of the cultivation, the tray 6 is moved to the colony observatory section by the reverse operation brought about the control signals $S_4$, $S_5$ and $S_6$.

At the colony observatory section, an image of colonies observed by a microscope-equipped TV camera is fed to the controller 25 as a measurement signal $T_1$ and, in the controller 25, the measurement signal $T_1$ is image-processed and the proportion of live cells present in the total picture of the colonies is calculated.

Through the above described process, desired kinds of cells or microorganisms resistant to the liquid culture used can be automatically selected from the cell solution or microorganism solution containing several kinds of cells or microorganisms.

Figure 6:
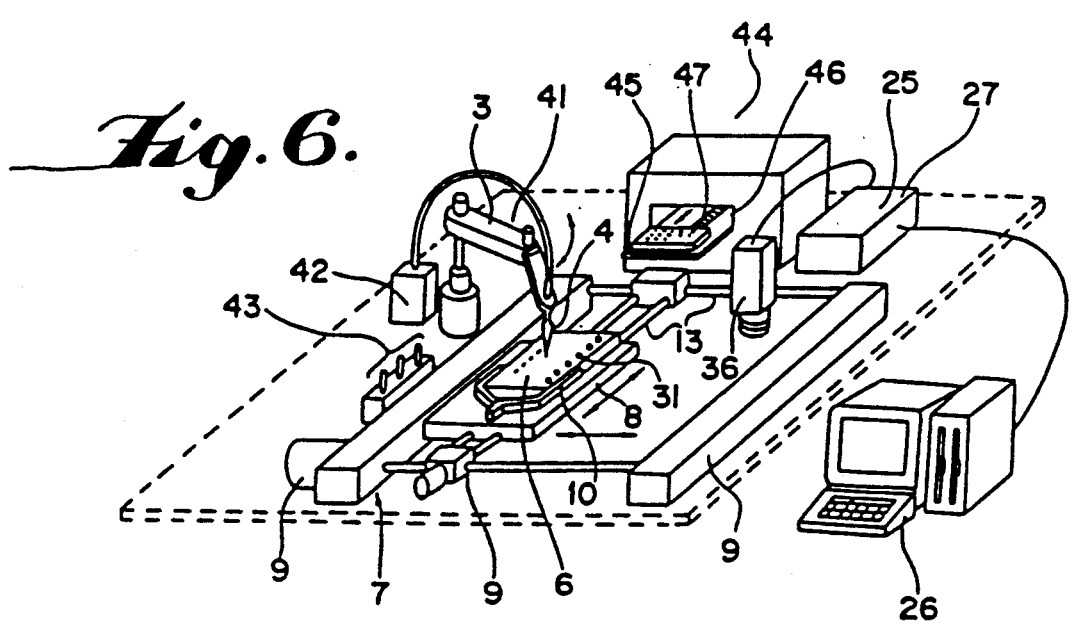
FIG. 6 is a perspective view of a second embodiment wherein the cell selecting section is comprised of an assay section.

EMBODIMENT 2

Where the cell selecting section in the present invention comprises an assay section, it is such as shown in FIG. 6, the operation of which is such as described below.

Figure 7:
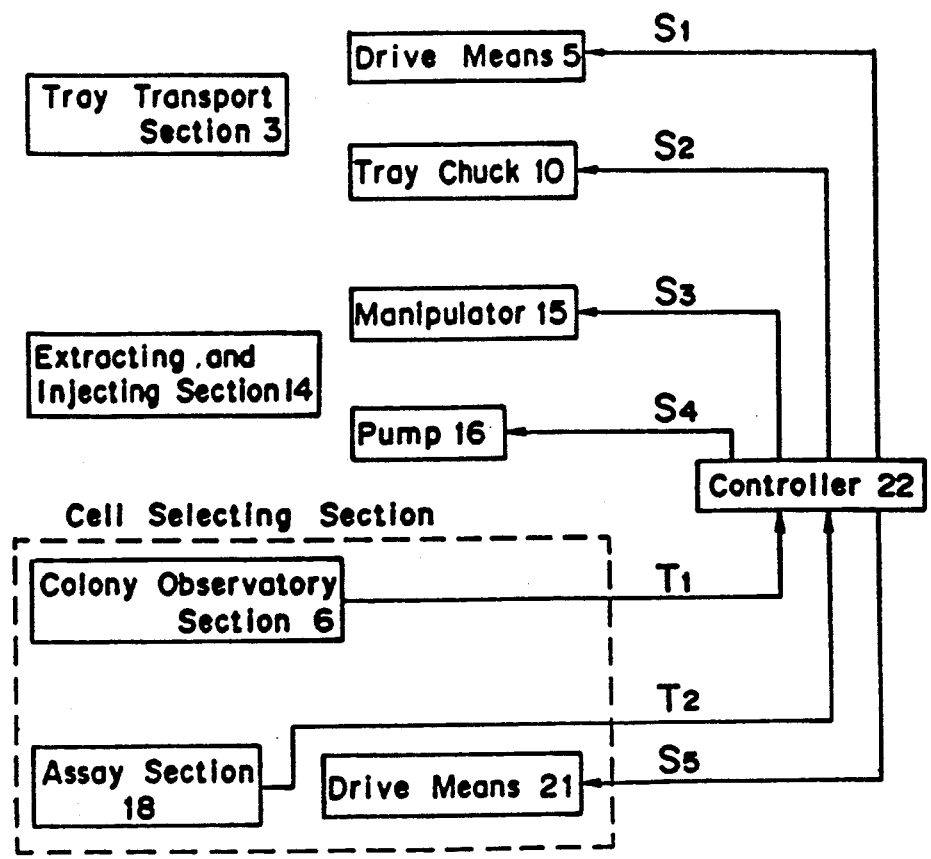
FIG. 7 is a block diagram of the second embodiment.
Figure 8:
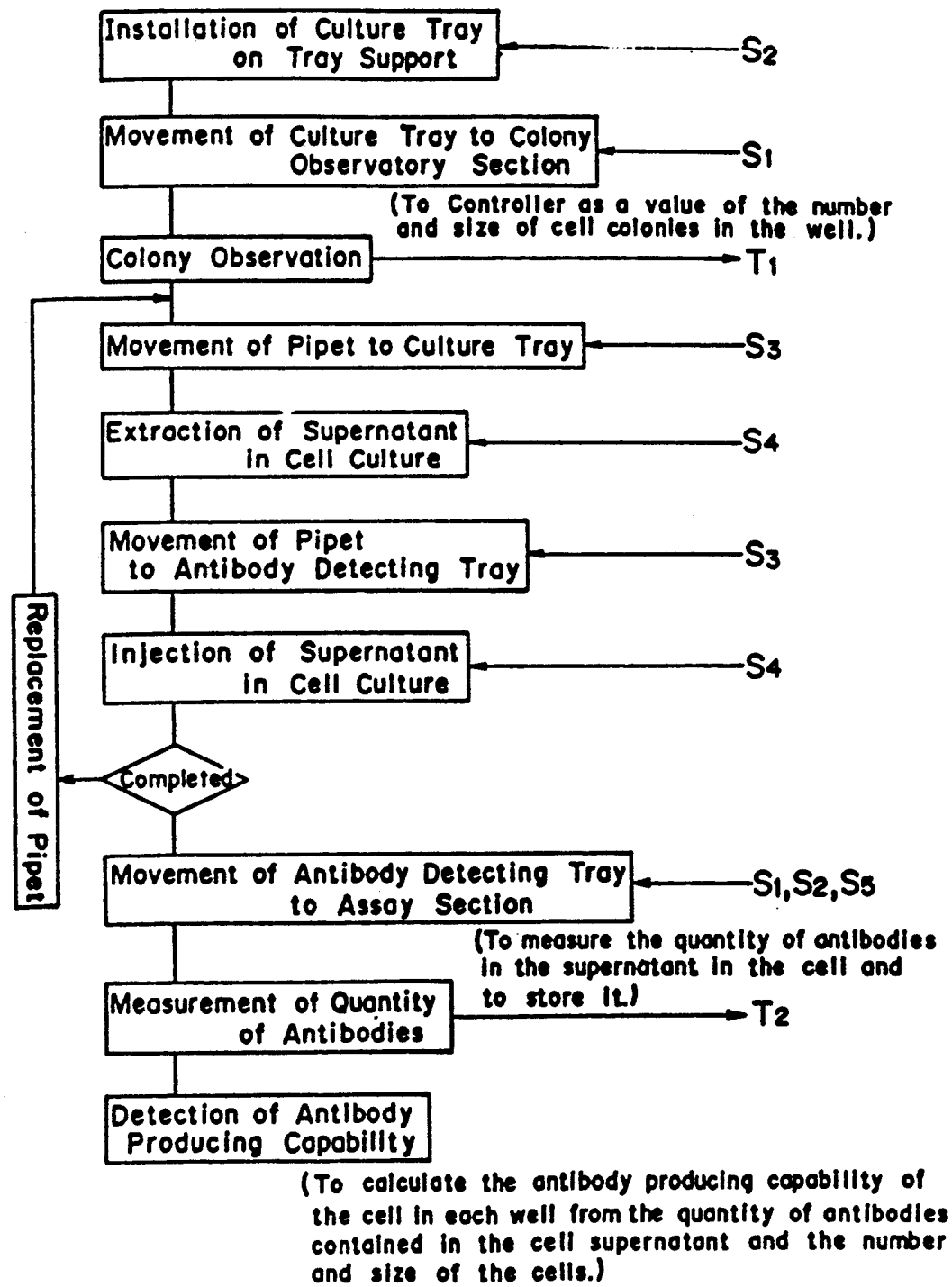
FIG. 8 is a flow diagram of the operation of the second embodiment.

A secretant producing capability detector device shown in FIG. 6 is a device comprised of a tray transport section, an extracting and injecting section, an assay section and a controller, wherein said tray transport section comprises a transport section tray support for the support thereon of a tray having a plurality of wells provided therein, and drive means for transporting said tray support to respective predetermined positions of said extracting and injecting section and the assay section, said extracting and injecting section comprises a manipulator for holding a pipette and for positioning said pipette above each well provided in the tray on the tray support and a pump for sucking and discharging a predetermined quantity of liquid into and from the pipette, and the controller is a device for controlling each said section as shown in FIGS. 7 and 8 according to operating conditions for each said section inputted thereto.

A cell fluid is filled in each well 31, and the tray 6 after having been cultivated in a $CO_2$ incubator is placed on the tray support 8 of the tray transport section 7. Where the number and size of colonies are desired to be observed, a colony observatory section 36 can be exceptionally provided, and, by the drive means 9 of the tray transport section 7, the tray support 8 is moved to a position where each well 31 provided in the tray 6 can be located below the colony observatory section 36.

A culture supernatant in each culture tray 6 of which the degree of proliferation of cells has been determined is sucked in a predetermined quantity by the pipette 4 moved by the manipulator 3 at the extracting and injecting section 41 and is injected into corresponding wells of an antibody detecting tray. The pipette manipulator 3 can employ an arm of horizontally articulated type, an arm of transverse type, etc. The pump 42 controls the quantity of suction and the quantity of discharge according to pressure and pressurizing time. At the time of extraction of the culture supernatant, the tip of the pipette 4 is used one time to avoid any contamination, and that once having touched is moved by the pipette manipulator 3 to a position of a pipette replacement section 43 and is replaced with new pipette by removing and fitting.

The antibody detecting tray 47 having the wells collected and injected from the corresponding wells of the culture tray 6 is placed on a tray support 45 at the assay section 44 and is transported to an antibody detecting position inside the assay section 44 by a drive means, comprising a feed screw 46 operated by a drive motor or a drive means comprising an air drive, at which position the quantity of antibodies contained in the supernatant in each of the wells is measured. The detector at the assay section 44 may be employed in the form of ELISA measuring apparatus or a liquid chromatograph.

Through the foregoing process, the degree of proliferation and the quantity of antibodies in each well are measured and from these values the antibody producing capability (=measured value of the quantity of antibodies/measured value of the degree of proliferation) of cells contained in each of the wells is automatically detected.

A block diagram and an operation flow diagram of Embodiment 2 are respectively shown in FIGS. 7 and 8. A measurement signal $T_1$ is indicative of the number, size and brightness of cell colonies in the well which have been image-processed, and a measurement signal $T_2$ is indicative of the quantity of antibodies contained in the cell supernatant. The quantity of the antibodies is stored in the controller and from this value the antibody producing capability of the cells contained in each cell is calculated.

In accordance with a control signal $S_2$, the culture tray 6 is placed on the tray support by the tray chuck, and in accordance with a control signal $S_1$, the culture tray 6 is moved to a position below a microscope-equipped TV camera at the colony observatory section.

Thereafter, the measurement signal $T_1$ from the colony observatory section, a control signal $S_3$ for controlling the operation of the manipulator, and a control signal $S_4$ for operating a pump for extracting and injecting the supernatant of the cell culture are identical in contents with those in Embodiment 1, and by the control signals $S_3$ and $S_4$, the pipette is replaced each time the supernatant of the cell culture is injected into each well of the antibody detecting tray.

After the injection of the supernatant of the cell culture into all of the wells of the antibody detecting tray has completed, the antibody detecting tray is moved onto the tray support 45 of the assay section by the control signals $S_1$ and $S_2$.

Subsequently, in accordance with the control signal $S_5$, the antibody detecting tray above the tray support 45 enters the assay section by the operation of a drive means. A measurement signal $T_1$ is indicative of the quantity of antibodies contained in the supernatant of the cell solution measured at the assay section and at the controller the antibody producing capability (=measured value of the quantity of antibody/measured value of the degree of proliferation) of the cells is calculated.

This apparatus is useable in the detection of the antibody producing capability and also in the detection of the capability of organisms secreting desired substances to produce the desired substance if the antibody detecting device is replaced with any other detecting device.

EMBODIMENT 3

The embodiment wherein the cell selecting section in the present invention comprises a cell number counting section and a cell isolating section is shown in FIG. 9.

A cell isolating device shown in FIGS. 9 and 10 is a device comprising an extracting and injecting section, a tray transport section, a cell number counting section, an isolating and injecting section and a controller, wherein the extracting and injecting section comprises a manipulator for holding a pipette and a pump for sucking and discharging a predetermined quantity of liquid into and from the pipette, the tray transport section comprises a tray support for the support thereon of a tray having a plurality of wells provided therein. And drive means for transporting the tray support to a predetermined position at each of the extracting and injecting section, the cell number counting section and the isolating and injecting section, and the controller is a device for controlling each said section as shown in FIGS. 11 and 12 according to operating conditions for each said section inputted thereto.

From target cells of a cell cultivating tray 6 wherein cells are proliferated, a cell solution is partially extracted into the pipette 4 moved by the pipette manipulator 3 and is dropped onto a glass plate 51. The glass plate 51 onto which the cell solution has been dropped is moved to a position below a microscope 54 by a drive motor 53 of a glass plate transport section 52. An image observed through the microscope 54 is fed to a control circuit 25 through a TV camera 55 and the number of cells is counted. Here, the cell number counting section 56 is comprised of, for example, the microscope 54, the TV camera 55, an input device 26 which also functions as a monitor for monitoring a part of the function of the control circuit 25, the glass plate 51 and the glass plate transport section 52. In the case where the number of cells thereof is greater than a predetermined value, the original cell solution is injected into a diluting vessel 61 by the use of the pipette 4 and the pipette manipulator 3 and a diluting liquid of a quantity determined by the number of the cells is added to dilute with the use of a diluting section. The cell solution so diluted is sucked by the cell isolating and injecting section 63. The diluted cell solution is sucked by the cell isolating and injecting section 63. The isolating and injecting section is, for example, of a construction shown in FIG. 10 and, while the diluting liquid which is an electrolyte flows through a thin tube 64, and in view of the fact that the resistance of the electrolyte flowing between electrodes varies with the presence of absence of cells, cells are detected in terms of the change in voltage measured. The tray transport section 7 with a tray 65 mounted thereon moves in synchronism with a cell detection signal and the cells detected are individually injected into the wells one in each well. It is to be noted that, in FIG. 10, 66 is cells, 67 is electrodes, 68 is an ammeter, and 69 is a well provided in the tray 65.

Figure 11:
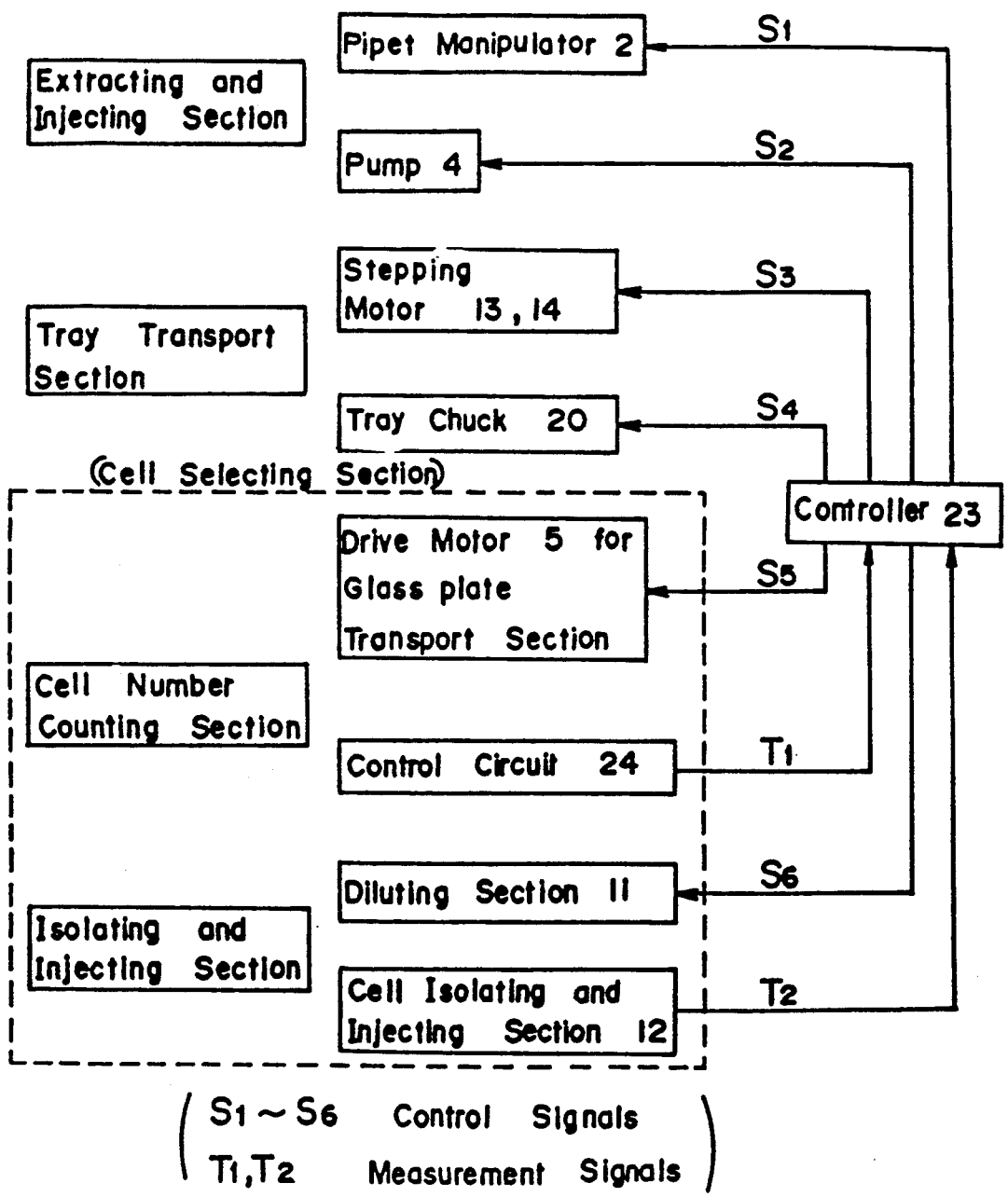
FIG. 11 is a block diagram of the third embodiment.
Figure 12:
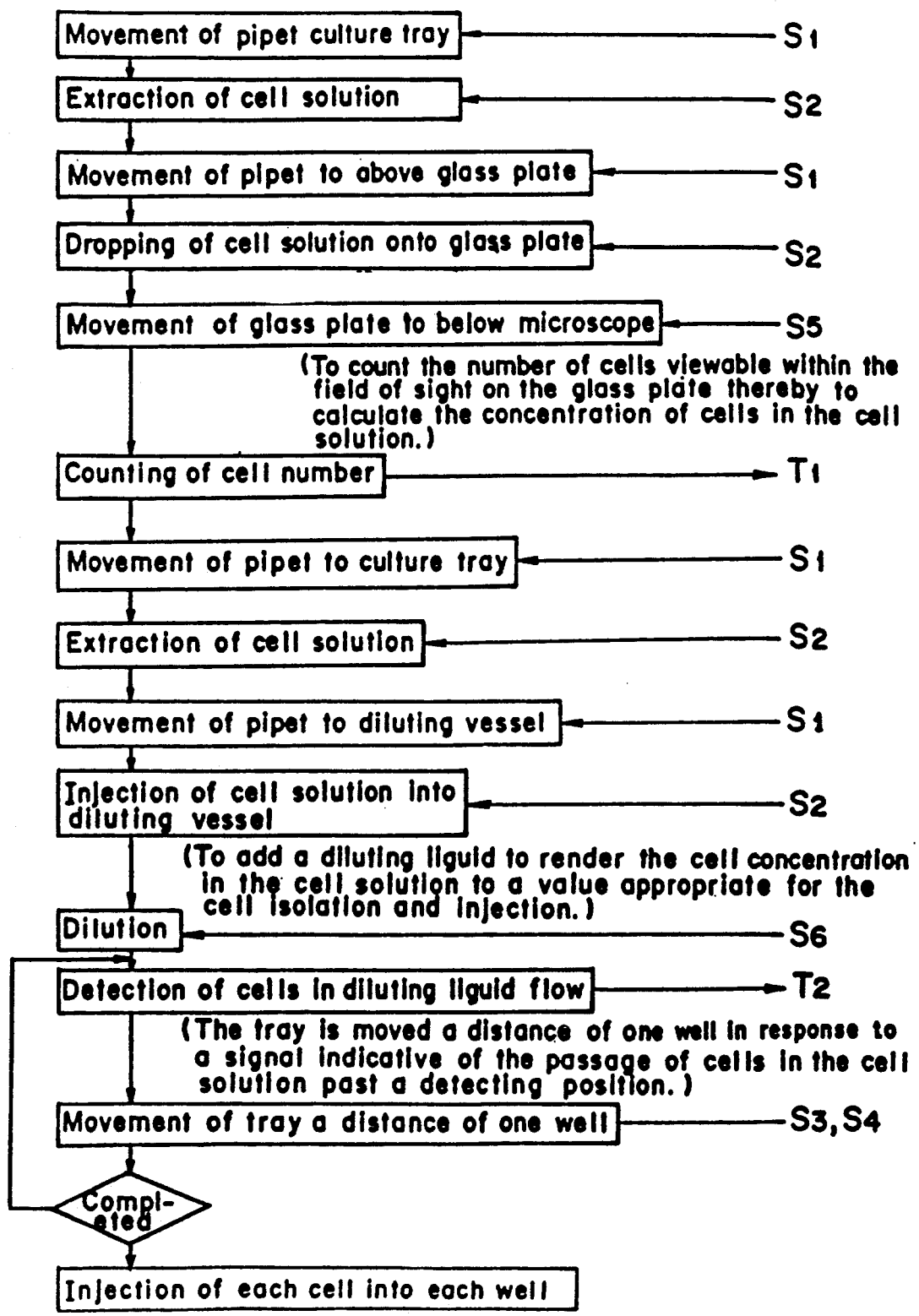
FIG. 12 is a flow diagram of the operation of the third embodiment.

The block diagram and the flow diagram of Embodiment 3 are respectively shown in FIGS. 11 and 12.

In response to a control signal $S_1$, the manipulator 3 is operated to move a pipette 4 grasped by the manipulator 3 to one of the wells on a culture tray, and in response to a control signal $S_2$, a pump is operated to extract the cell solution in each well. Thereafter, in response to the control signal $S_1$, the manipulator 3 is operated to move the pipette 4 to a position above the glass plate 51 and, in response to the control signal $S_2$, the cell solution in the pipette 4 is dropped onto the glass plate 51.

This control signal $S_5$ is a signal for controlling the start and stop of a drive motor at the glass plate transport section, and in response to the control signal $S_5$, the glass plate 51 is moved to a position below a microscope 54 to enable the cell number counting section to count the number of cells in the cell solution. The measurement signal $T_1$ is indicative of the number of the cells, the value of which calculates the concentration of the cells in the cell solution at the controller. Where the cell concentration is higher than a predetermined value, in response to the control signal $S_1$, the pipette of the manipulator 3 is moved to the well containing the cell solution of such cell concentration and, in response to the signal $S_3$, a pump is operated to extract the cell solution into the pipette. Subsequently, the pipette having extracted the cell solution is moved to a diluting container in response to the control signal $S_1$, and in response to the control signal $S_2$, the cell solution is filled into the diluting container, and in response to a control signal $S_6$, a diluting liquid is added to the diluting container to dilute to the concentration lower than the predetermined value so that the cell concentration in the cell solution can be adjusted to a concentration appropriate to the isolation and injection.

The diluted cell solution is sucked into the cell isolating and injecting section 63, and when the cells pass through the thin tube 64, the measurement signal $T_2$ is generated.

The measurement signal $T_2$ is a signal indicative of the passage of the cells in the diluted cell solution past a detecting position of the cell isolating and injecting section, and in synchronism with this signal, the tray transport section is operated in response to the control signal $S_3$ and $S_4$ to move a distance corresponding to the space between the wells on the tray at the outlet of a liquid feed tube 70.

Through the foregoing process by the cell selecting apparataus of the present invention, the cells can be individually isolated one by one out from the cells.

With the use of this apparatus, assurance can be obtained that the antibody obtained is a monoclone and, unlike the selection of the monoclonal antibody producing cells according to the limited dilution, the proliferation need not be repeated several times and it is possible to select the monoclonal antibody cells in a reduced period of time.

EMBODIMENT 4

The embodiment wherein the cell selecting section in the present invention comprises a cultivating section, a colony observatory section, an assay section and a cell isolating section is shown in FIG. 13.

Figure 16:
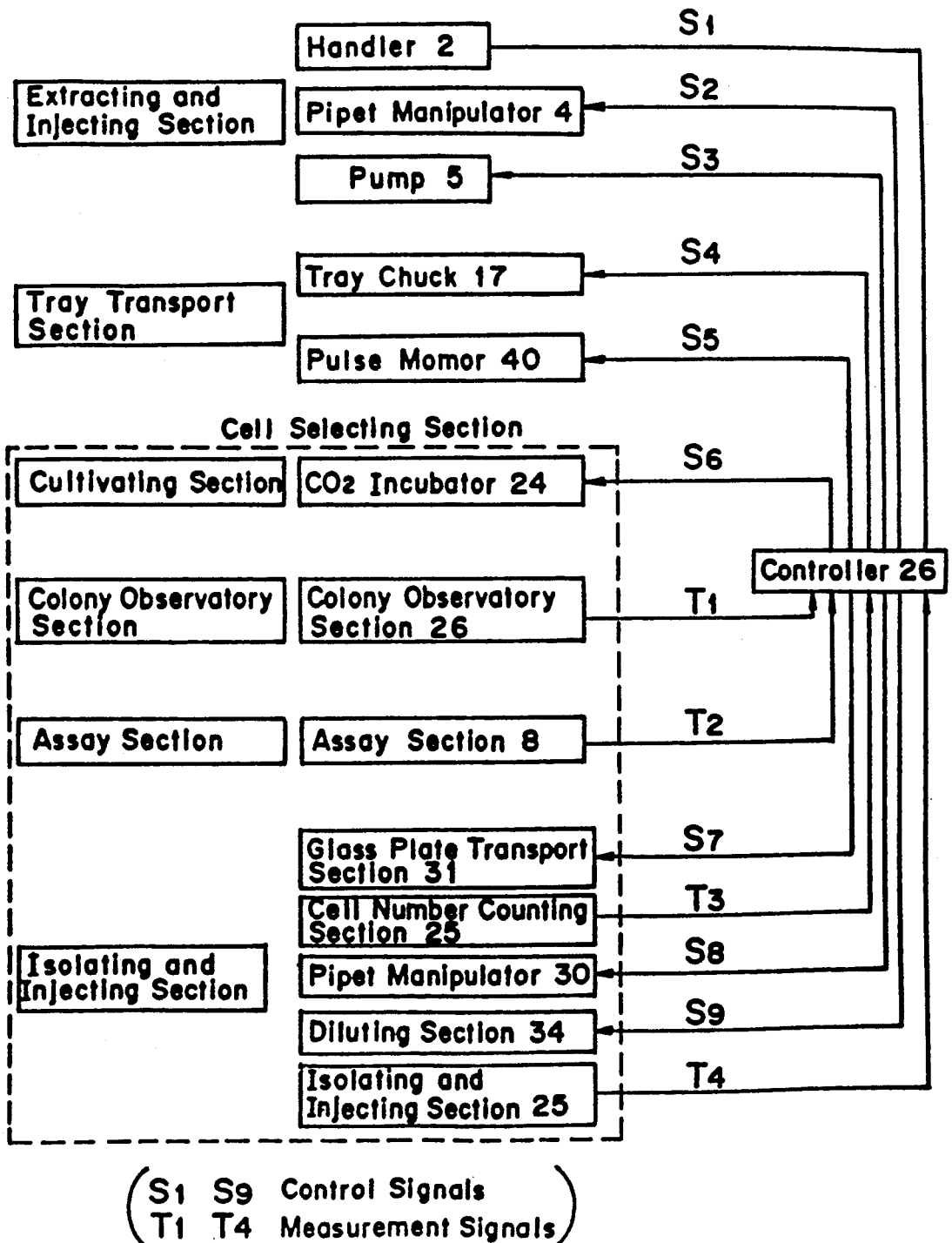
FIG. 16 is a block diagram of the fourth embodiment.
Figure 17A:
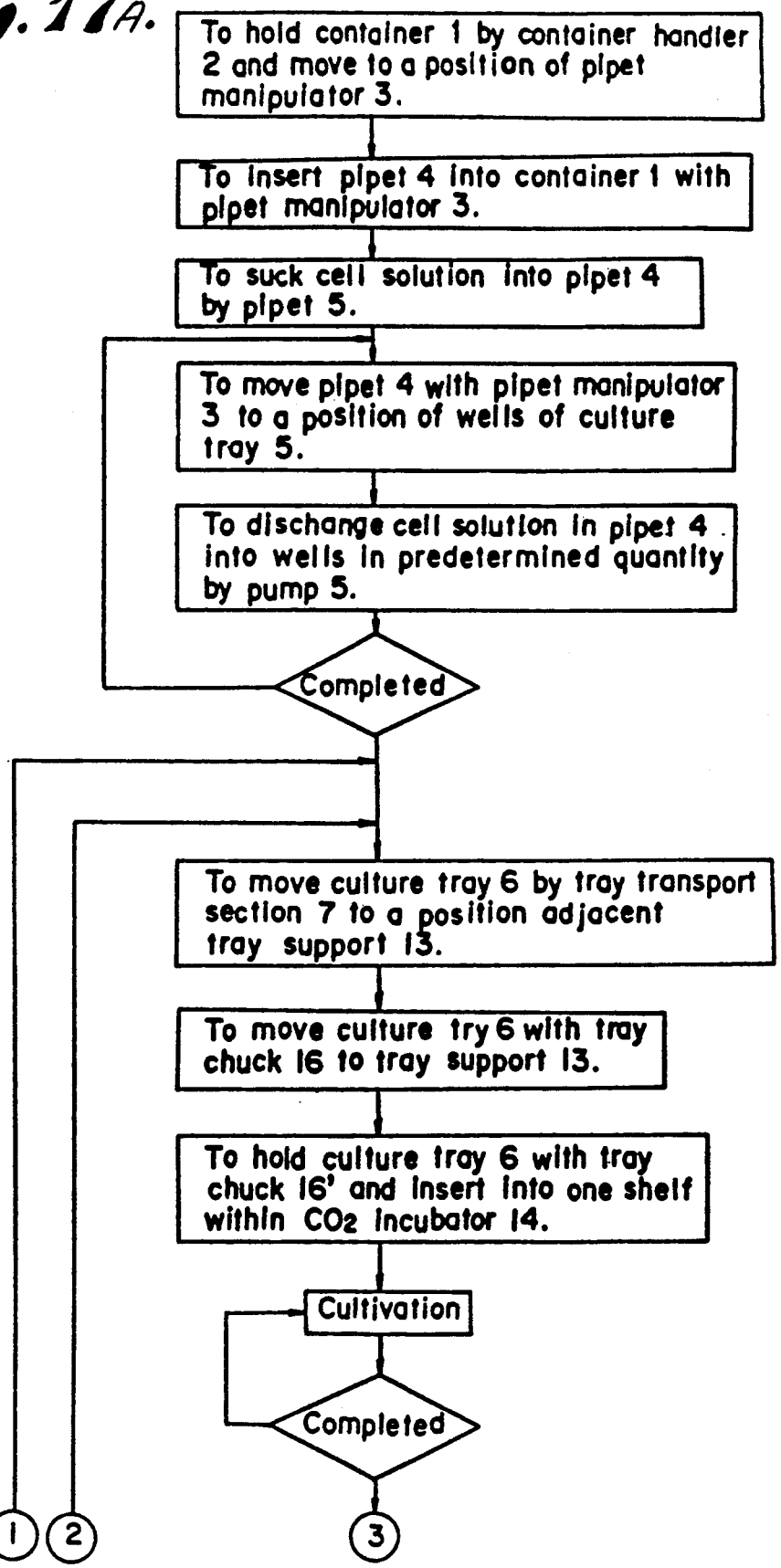
FIG. 17A-17E is a flow diagram of the operation of the fourth embodiment.
Figure 17B:
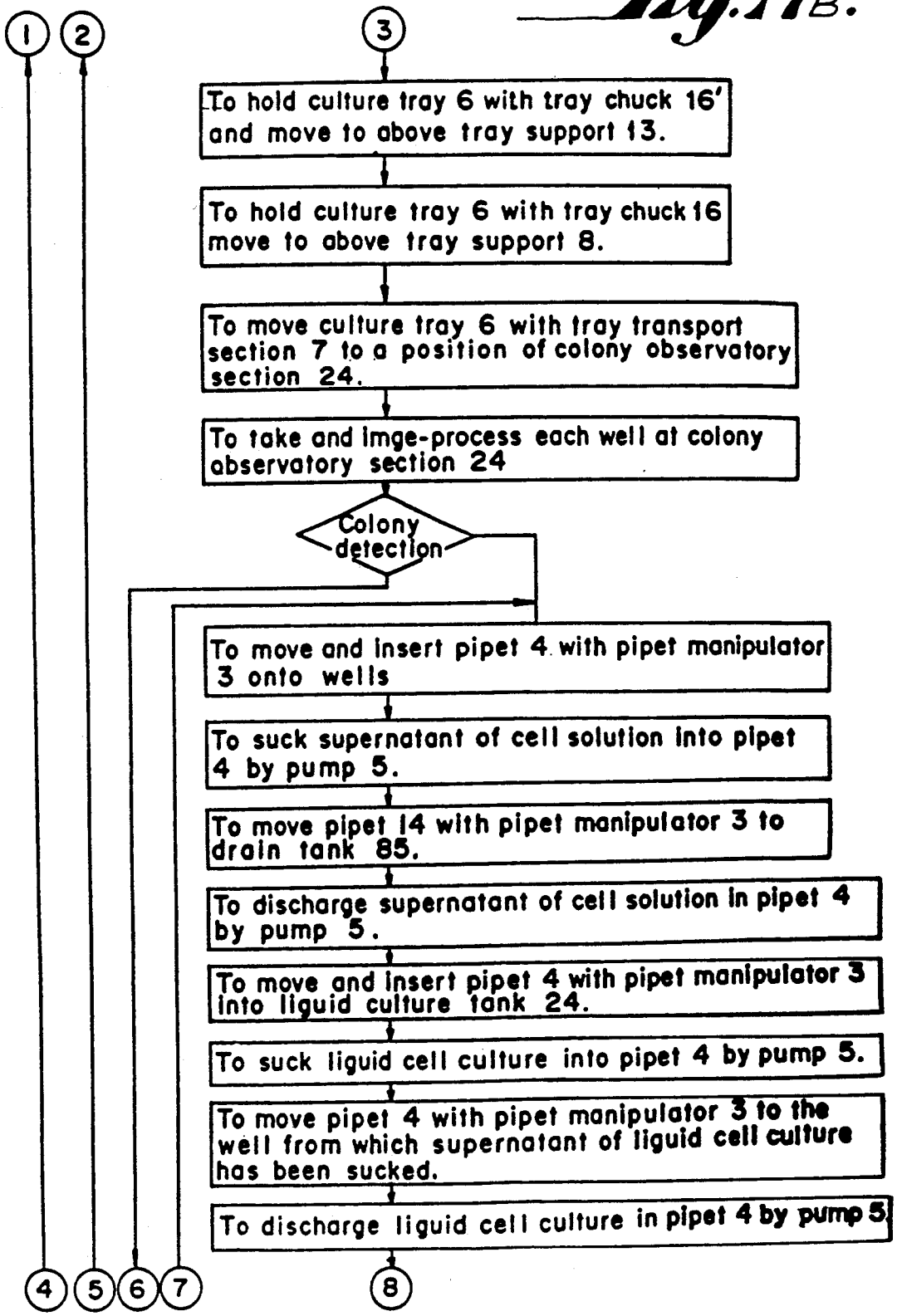
Figure 17C:
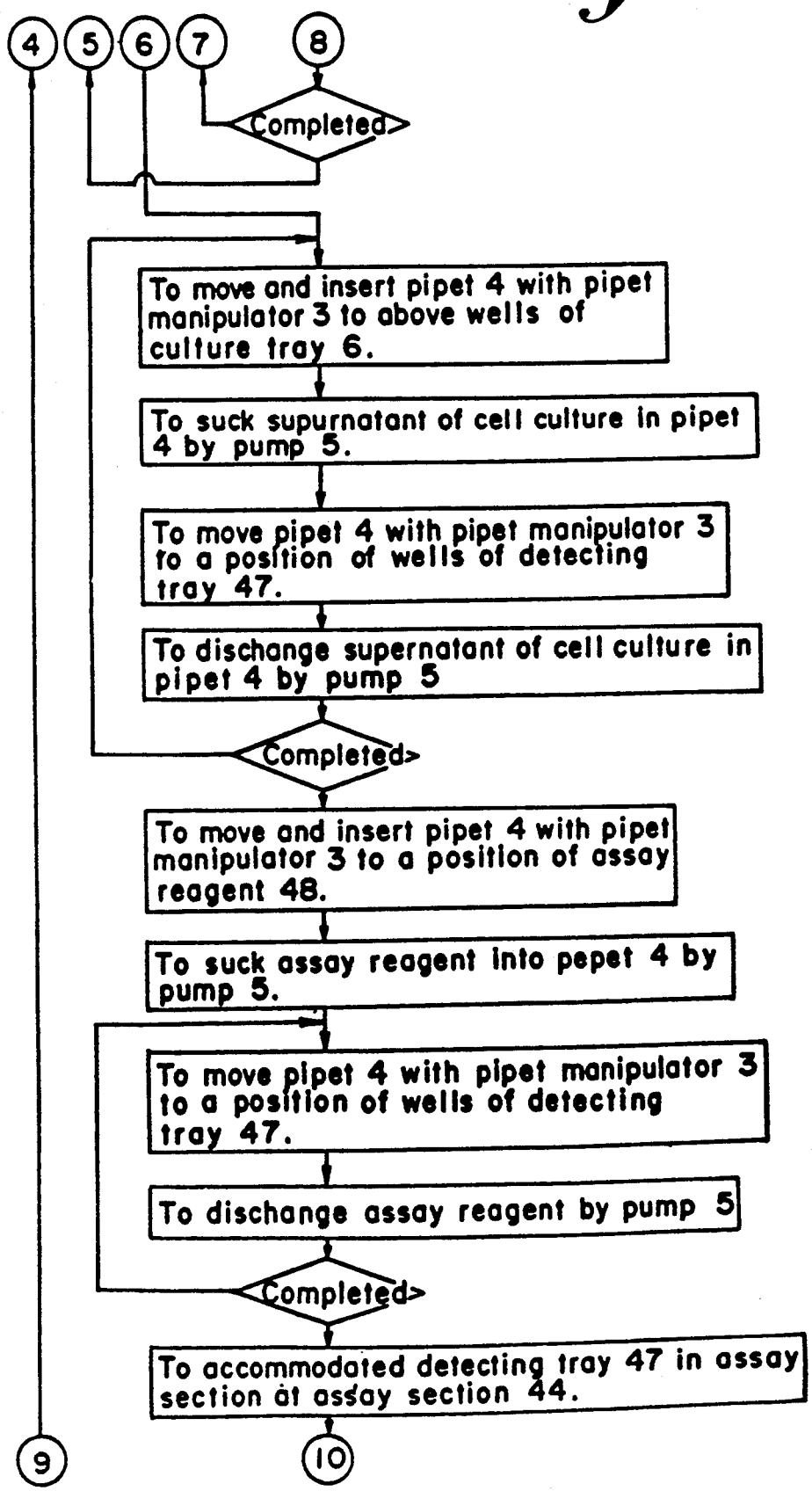
Figure 17D:
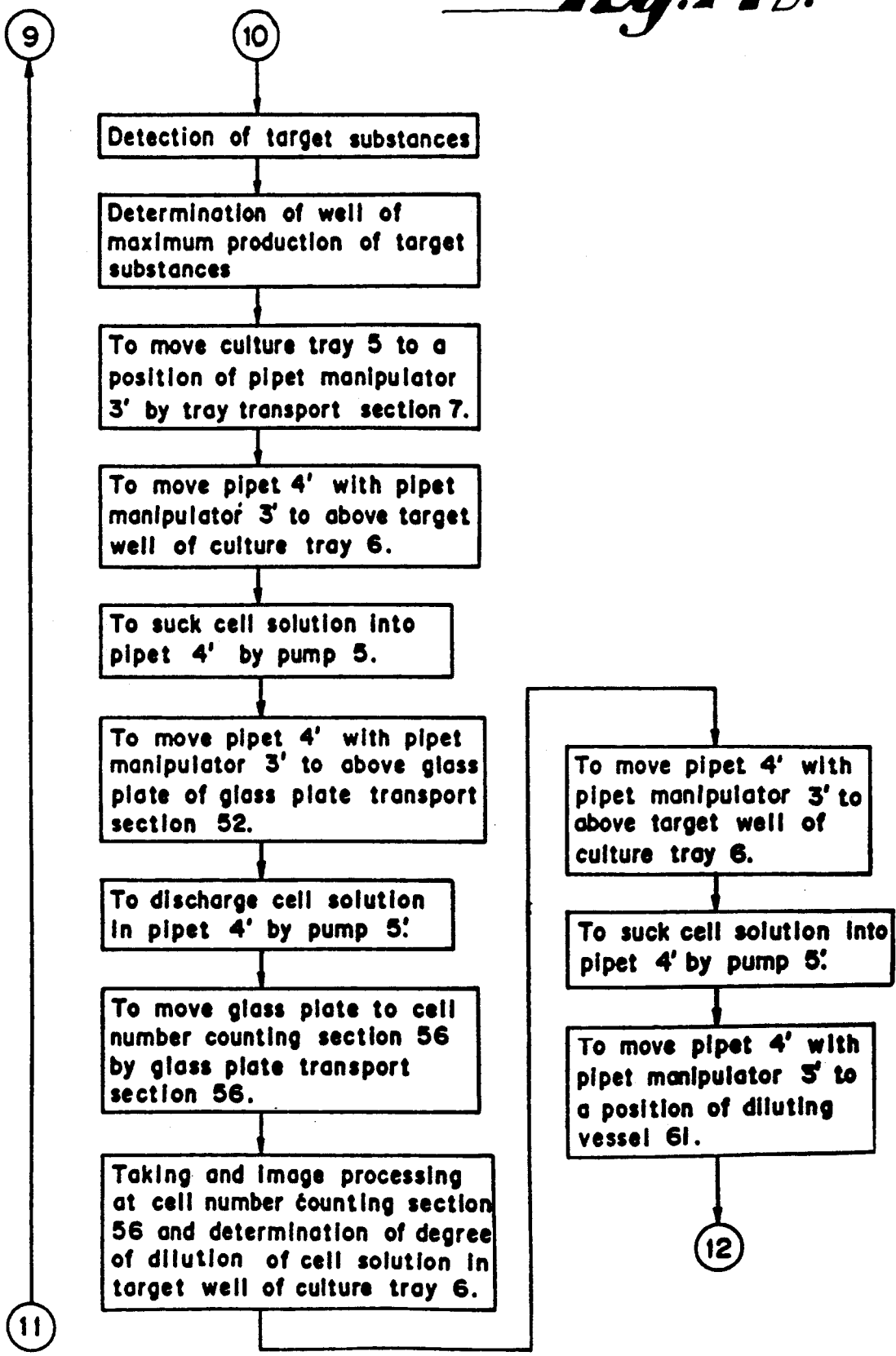
Figure 17E:
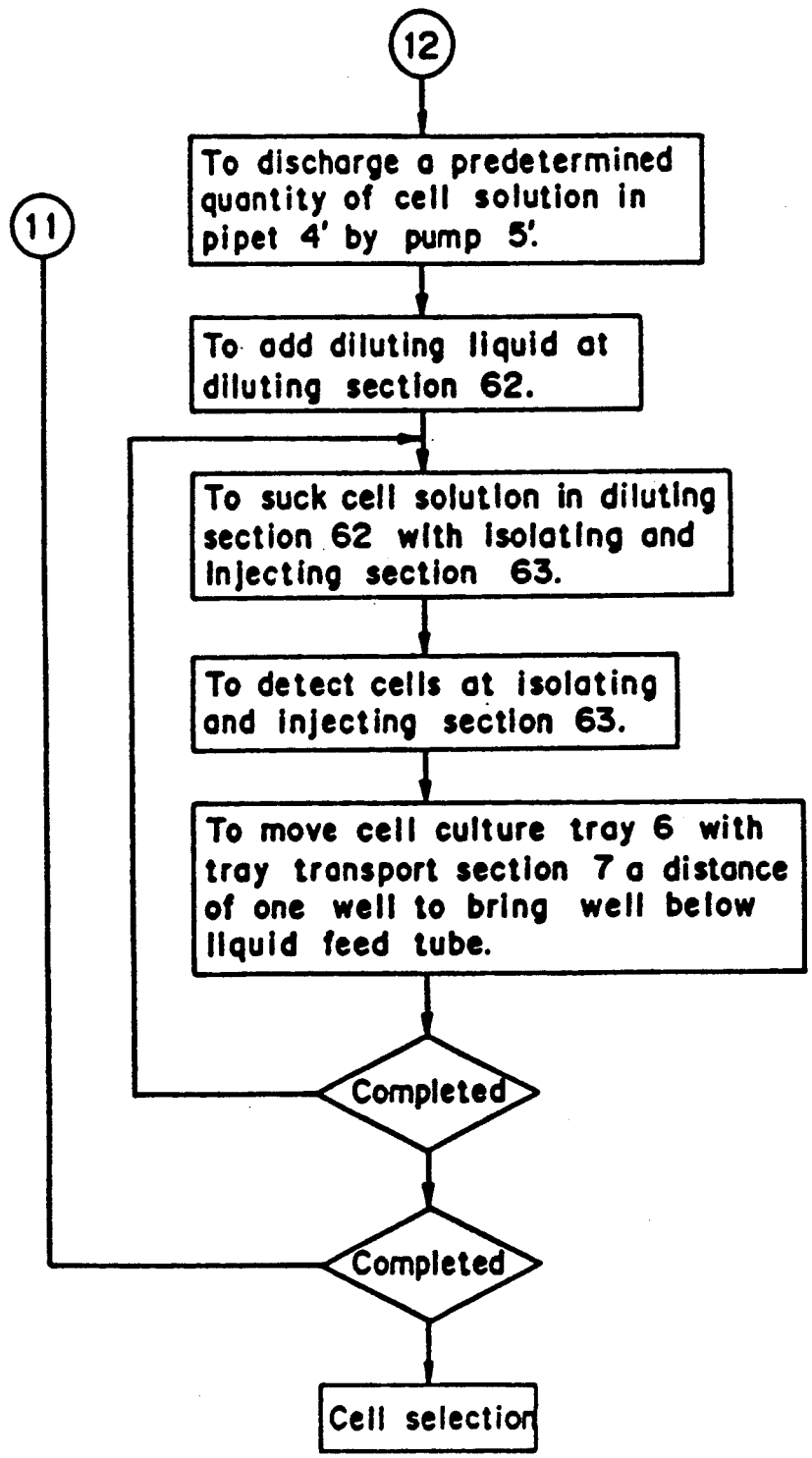

The cell selecting apparatus shown in FIGS. 13, 14 and 15 is a device comprised of an extracting and injecting section, a tray transport section, an assay section, an isolating and injecting section and a controller, wherein the extracting and injecting section comprises a pipette, a manipulator for holding the pipette, and a pump for sucking and discharging a predetermined quantity of liquid into and from the pipette, said tray transport section comprises a tray support for the support thereon of a tray, and drive means for transporting the tray support to predetermined positions of the extracting and injecting section, the cultivating section, the assay section and the isolating and injecting section, the cultivating section is provided with a traystock for accommodating a plurality of the trays, and the controller is a device for controlling each said section as shown in FIGS. 16 and 17 according to operating conditions for each said section inputted thereto.

Figure 18:
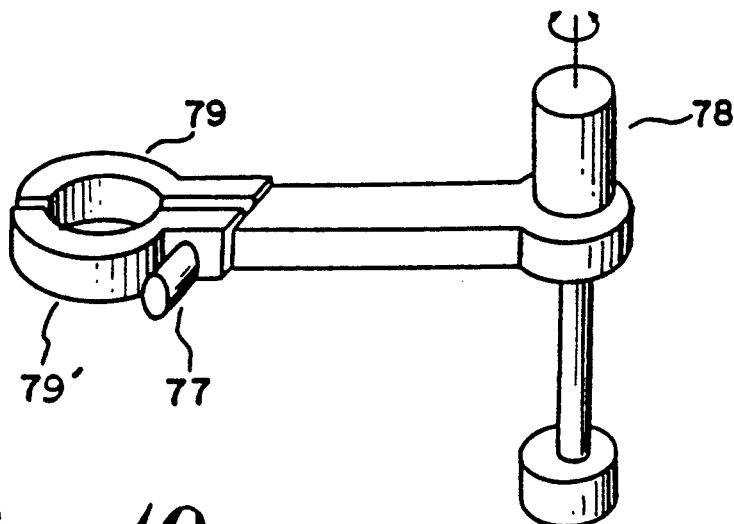
FIG. 18 is a perspective view of a container handler.
Figure 19:
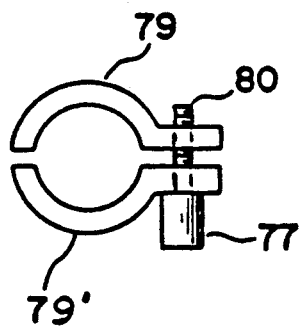
FIG. 19 is a plan view of a chuck of the container handler.

A container, such as, for example, a tube, containing fused cells and a liquid culture is grasped by a conatiner handler 2, and the container 1 is moved to a position of a pipette manipulator 3. The csontainer handler 2 is contructed according to the prior art, and the tip of the container handler 2, a concrete example of which is shown is Fig. 18, has chucks 79 and 79', adapted to be driven by a motor 77, fitted thereto. FIG. 19 is a sectional view of a chuck portion, and the chucks 79 and 79' are coupled with the motor 77 by means of a feed screw 80 threaded in opposite directions with respect to each other and are controlled its closure and opening depending on the direction of rotation of the motor 77. Also, the rotation of the container handler 2 is controlled by a motor 78. The dotted line at the container handler 2 in FIG. 13 is a phantom line when moved to a position of the pipette manipulator 3.

Figure 20:
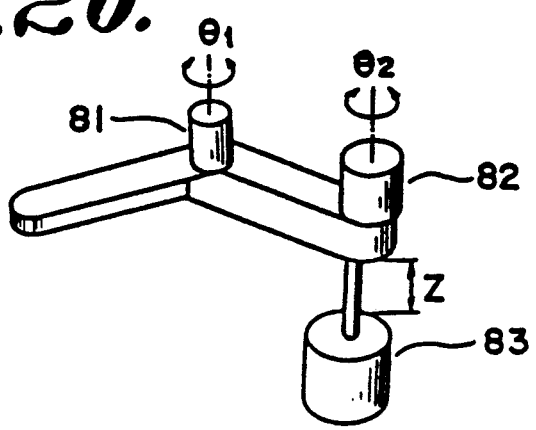
FIG. 20 is a perspective view of a pipette manipulator.

The pipette manipulator 3 is also constructed according to the prior art, a concrete example of which is shown in FIG. 20. 81 and 82 are motors, imparting a rotation about $\theta_1$ axis and $\theta_2$ axis. Also, a manipulator leg portion 83 is accommodated with a motor and rack-and-pinion for controlling the movement of the whole manipulator in a Z direction. These controls are all performed by a controller 25.

By rotating the motor in the manipulator leg portion 83, the pipette manipulator 3 is lowered to insert the pipette 4 fitted to the tip, into the container 1 to permit the pump 5 to suck the cell solution. The pump 5 is, for example, PERISTER pump, and by causing the controller 25 to control the time of rotation of the pump, the quantity to be sucked is controlled. Subsequently, the drive motors 81 and 82 are rotated to control the manipulator 3 to move the pipette 4 at the tip to a positon of a certain well on the culture tray 6, and the pump 5 is used to discharge a predetermined quantity of the cell solution into the well. The discharge is possible by rotating the PERISTER pump 5 in the reverse direction during the suction, and the quantity of discharge can be controlled by the time of rotation of the pump 5. The tray transport section 7 is a general X-Y moving mechanism and operable to move and control the transport section tray support 8 provided with a tray chuck 16 to an arbitrary position on an X-Y plane. After each well has been moved to a position immediately below the pipette 4 by controlling the tray transport section 7, the pump is similarly controlled as to the time to discharge a predetermined quantity of cell solution into a predetermined number of wells of the tray. The operation of the tray transport unit 7 may employ drive means such as a motor drive as shown in FIG. 14 or a gear drive as shown in FIG. 15. In FIG. 14, 71 is a feed screw (ball screw), and 72 is a pulse motor, and by rotating the pulse motor, the transport section tray support 8 is horizontally moved, the control of the position of which is carried out according to the number of drive pulses for the pulse motor. In FIG. 15, 73 is an air cylinder, 74 is an electromagnetic brake, 75 is a potentiometer, and 76 and 76' are electromagnetic valves, and by controlling the valves 76 and 76', an air is introduced into the cylinder to move the transport section tray support 8, the position of which is detected by the potentiometer 75, and after it has been moved to a predetermined position, it is brought to a halt by the electromagnetic brake 74. By arranging the mechanisms of FIG. 14 or FIG. 15 transverse to each other, the X-Y moving meschanism can be constructed.

The culture tray 6 having the solution injected is accomodated in the tray stock 15 within the $CO_2$ incubator 14 through the tray support 13 and maintained for a predetermined period of time in a cell cultivating atmosphere.

The transport section tray 8 and the tray support 13 are fitted with tray chucks 16 and 16' shown in FIG. 3. Describing with reference to FIG. 13, in order for the culture tray 6 to be accommodated in the tray stock 15, the culture tray 6 is moved by the tray transport section 7 to a position adjacent the tray support 13. Then, the tray chuck 16' of the tray support 13 is lowered from above the tray support and the tray chuck 16 is subsequently moved in the X direction shown in FIG. 3 to convey the tray 6 onto the tray support 13. Further, the tray 6 is removed from the tray chuck 16 and the tray chuck 16 is returned to above the transport section tray support 8. Thereafter, the tray chuck 16' is raised to grasp the tray 6. Further, the tray chuck 16' is moved to insert the tray 6 onto one of the shelves of the tray stock 15. By removing the tray 6 from the tray chuck 16' and retracting the tray chuck 16', the accommodation of the tray 6 into the $CO_2$ incubator 14 is completed. The $CO_2$ incubator 14 is provided, as shown by the dotted line in FIG. 2, with a closing and opening door 14' according to the prior art, and the door is opened and closed incident to the loading and unloading of the tray 6. The tray stock 15 is composed of accommodation shelves, a feed screw 22 for moving them up and down, and a drive motor 23.

The culture tray 6 which has been retained for the predetermined period of time in the cell cultivating atmosphere within the $CO_2$ incubator 14 is moved to the tray transport section by the operation reverse to that during the insertion into the tray stock 15, and each well on the culture tray 6 is moved to a postion of the colony observatory section 24 for the detection of whether or not the colonies have been proliferated.

This colony observatory section 24 is comprised of an image input section including a microscope-equipped TV camera, and an image processing section which is a computer, and an image processing is effected digitally to an enlarged image taken at the input section to detect the colonies. As an image processing method, the live cells are detected on a binary coded scheme by the utilization of the fact that the brightness of a portion of the live cells is high, and from the proportion occupied by the live cells within the total picture, the colonies can be detected. In the event that no colony is detected with respect to all of the wells of the tray 6, the supernatant of the cell solution, that is, the exhausted liquid cullture, is sucked by the pipette 4 then moved by the pipette manipulator 3, and the pipette manipulator 3 is further moved and the sucked liquid culture is discarded into a drain tank 85. Subsequently, the pipette maniplulator is similarly moved to suck a fresh liquid culture from a culture liquid tank 84, and by discharging it into the well from which the exhausted liquid culture has been sucked, the replacement of the liquid culture is accomplished. The foregoing procedure is carried out to all of the wells being cultivated, and again by the described operation, the tray 6 is loaded into the tray stock 15 within the $CO_2$ incubator 14 for the continuance of the cultivation for the predetermined period of time. On the other hand, in the event that a colony is detected, the supernatant of the cell solution is sucked into the pipette 4 moved by the pipette manipulator 3 from each well of the culture tray 6 and is discharged onto the well of the detecting tray. This is carried out to all of the well. Further, by the use of the pipette manipulator 3, a predetermined quantity of assay reagent 48 is added to each well on the detecting tray 47 filled with the cell solution supernatant, and the detecting tray 47 is moved by a motor drive according to the prior art to the Assay Section 44 whereat the detection is made to find whether or not the target substance is contained in the cell solution supernatant filled in each well of the detecting tray 47.

As the assay section, there is ELISA. The fact that the target substance has been detected as contained in the cell solution supernatant means that the cells in the well of the original culture tray 6 are producing the target subject. With respect to the cell solution producing the greatest quantity of the target substances of the wells of the culture tray 6 producing the target substances, a portion thereof is injected by a pipette manipulator 3' onto a glass plate at a glass plate transport section 52 and, thus, the number of the cells contained in the cell solution on the glass plate is counted by the cell number counting section 56. The pipette manipulator 3 is similar to the pipette manipulator 3 and has its tip provided with a pipette 4' and a PERISTER pump communicated therewith. The glass plate transport section 52 is a linear motion mechanism comprised of a drive motor and a feed screw and is beforehand mounted on a movable stage by the glass plate 51. The cell number counting section 56 comprises an image input section including a microscope-equipped TV camera and an image processing section which is a computer and is operable to count the number of live cell on a digital scheme as is the case with the colony observatory section 24. Since the position of the glass plate at which the cell solution in the culture tray 6 is injected onto the glass plate 51 differs from that at which the counting is performed by the cell number counting section 56, this is controlled at the glass plate transport section 52.

Based on the number of the cells counted by the cell number counting section 56, the concentration of the cells in the cell solution in the wells of the original culture tray 6 to determine the degree of dilution to which it is diluted to a predetermined concentration enough to perform the isolation and injection, and a predetermined quantity of the cell solution in the wells is injected by the pipette manipulator 3' into a constant quantity diluting vessel 61 wherefor a predtermined quantity of diluting liquid is added by the diluting section 62 to achieve the desired concentration.

The cell concentration is calculated by the following method. That is, while the quantity of the cell solution in the wells and the sampling quantity on the glass plate 51 are fixed, it is calculated backwards from the number of the cells on the glass plate in terms of volume ratio. The diluting section 62 is composed of a diluting liquid tank and a pump, and by the time control of the pump the quantity of the diluting liquid to be discharged is controlled.

The diluted cell solution is sucked by the isolating and injecting section 63. The isolating and injecting section has such a cross-sectional construction as shown in FIG. 10 and, in the isolating and injecting section, the diluting liquid which is an electrolyte flows in a thin tube 64 and, by the utilization of the fact that the resistance of the electrolyte flowing between electrodes 67 differs depending on the presence of absensce of the cells, the cells are detected in terms of the change in current value.

The detection of the cells can be accomplished by providing a light emitter and a light receiver, instead of the electrode, on respective sides of the thin tube and sensing with the light receiver the interception of light from the light emitter resulting the passage of the cells.

The isolating and injecting section 63 is composed of a suction pump 86, and the above described cell detecting, sections 67 and 68, and in the event that no cell is detected, the diluting liquid is discarded, but in the event that the cells are detected, the culture tray 6 is moved by the tray transport section 7 in synchronism with a signal indicative of the detection of the cells and the cells are injected one by one into each well of the culture tray 6 which are not used for cultivation.

This sets the volume of a liquid feed tube 70 from the cell detecting section to the well to a value smaller than the volume of the well and, at the time the signal indicative of the detection of the cell is obtained, the suction pump of the isolating and injecting section 63 is temporarily brought to a halt. Then, the tray transport section 7 is driven, and after the wells into which the cells are to be injected have been moved to a position immediately below the liquid feed tube, the suction pump is again driven to inject the cells into the wells. In this case, if two or more cells are present within the liquid feed tube from the cell detecting section to the well, one cell cannot be injected into one well, and in order to avoid the occurrence of such situation, a necessary and sufficient dilution is performed in the diluting vessel 61. This value is empirically determined beforehand.

The culture tray into which the cells have been injected one by one is again accommodated in the tray stock 20 within the $CO_2$ incubator to cultivate the cells.

In a way similar to that described hereinbefore, the detection of the target substances is carried out, and through the foregoing process the desired cells are selected.

A block diagram and a flow diagram of Embodiment 4 are respectively shown in FIG. 14 and FIG. 15.

The container 1 is grasped by the container handler 2, a process from the movement of the container 1 to the pipette manipulator 3 to the discharge of the cell solution into each well in a predetermined quantity by the pipette and a process from the movement of the culture tray 6 to a position adjacent the tray support 13 at the cultivating section by the tray transport section 7 to the movement to a position of the colony observatory section subsequent to the completion of the cultivation are controlled by control signals $S_1$ to $S_4$ in a manner similar to that in the Example 1. A measurement signal $T_1$ from the colony observatory section is a signal similar to that in Embodiment 1.

Then, the pipette 4 is moved by the manipulator 3 to the well at which colonies have been observed, and the repetition of a process from the suction of the cell solution supernatant to the discharge thereof into each well of the detecting tray 47 is carried out by the control signals $S_2$ and $S_3$ for controlling the manipulator of the extracting and injecting section and the signals $S_4$ and $S_5$ for controlling the tray transport section.

Subsequently, a series of operation up until the assay reagent is discharged into the wells of the detecting tray 47 is controlled by signals ($S_4$ to $S_5$) similar in intelligence to the control signal $S_5$ in Embodiment 2.

Further, a series of operation wherein in the cell number counting section the number of the cells in the cell solution is counted and in the cell isolating section the cells are isolated from each other in each well is controlled by signals ($S_3$ and $S_7$ to $S_9$) similar in intelligence to the control signals ($S_1$ to $S_8$) in Embodiment 3.

INDUSTRIAL APPLICABILITY

The present invention is such that, in the case where desired cells or microorganisms, for example, monoclonal antibody producing cells are to be selected from the cell solution or microorganism solution containing several kinds of cells or microorganisms, it is necessary to select the cells having a high capability of producing antibodies. With the apparatus of the present invention, it is possible to assuredly detect wells, containing the cells capable of proliferating in a short time and having a high antibody producing capability, from the liquid culture of a huge number of cells that can not be handled manually. In addition, since the handling of the cells is carried out within the apparatus which is a sterile environment, the possibility of contamination by the various germs is minimized and the desired cells can be steadily detected, wherefor the selection is possible.

From the foregoing, the monoclonal antibodies can be efficiently obtained, and it is evident that contribution can be made to the application of the monoclonal antibodies.

What is claimed is:

1. A cell selecting apparatus, comprising:
   an extracting and injecting section;
   a tray transport section for transporting at least one tray having a plurality of wells;
   a controller; and a
   cell selecting section,
   wherein said extracting and injecting section comprises a pipette, a manipulator for holding and moving said pipette up and down at a predetermined position above a culture tray and a pump for drawing and discharging a predetermined quantity of a liquid culture into and from said pipette, said tray transport section comprises a transport section tray support for the support thereon of the culture tray provided with a plurality of wells therein, a first tray chuck and a first drive means for transporting said transport section tray support to predetermined positions with respect to said extracting and injecting section, said cell selecting section comprises a cultivating section and a colony observatory section, wherein said cultivating section comprises an incubator including a tray stock for accommodating a plurality of trays, a second tray chuck and a second drive means for moving said stock and a cultivating section tray support for transporting cultivating trays to said tray stock, and further said cultivating section being operable to interact with said extracting and injecting section in a manner such that said pipette can be manipulated to a predetermined position at which location said liquid culture may be injected into or extracted from a cell colony without disturbing the growth of said cell colony, and said controller comprises a device which generates and transmits at least eight control signals for controlling each of said sections according to operating conditions of each of said sections inputted thereto, whereby said sections of said cell selecting apparatus operably interrelate and communicate sequentially in steps including, (a) in response to a first signal and a second signal, moving said pipette to a position with respect to a container of cell solution so that, upon activation, said pump extracts a quantity of said cell solution from the container via said pipette, (b) in further response to said second signal, moving said pipette to a position above a well of a designated culture tray, (c) in response to a third signal, activating said pump to inject said cell solution contained in said pipette into a well of the designated culture tray, (d) in response to a fourth signal, moving the designated culture tray a distance corresponding to one of said wells, (e) in response to said fourth signal and a fifth signal, sixth signal and seventh signal, transferring the designated culture tray to a position within said incubator of said cultivating section, (f) in response to an eight signal, providing a growth environment within said cultivating section as designated by parameter input to said controller, and (g) in further response to said fourth, fifth, sixth and seventh signals, moving the designated culture tray to said colony observatory section, and in response to a first measurement signal from said colony observatory section, calculating as a value, the number and size of said cell colonies which have been processed.

2. The cell selecting apparatus as defined in claim 1 wherein said colony observatory section comprises:

a TV carmera, and a control circuit for converting into an electric signal a surface area occupied by colonies whose image has been received by said TV camera.

3. A cell selecting apparatus, comprising:

a tray transport section for transporting at least one tray;

an extracting and injecting section;

a cell selecting section; and a controller, wherein said tray transport section comprises a transport section tray support for supporting thereon a culture tray provided with a plurality of wells therein, a tray chuck and a first drive means for transporting said tray support to predetermined positions with respect to said extracting and injecting section and said cell selecting section, said extracting and injecting section comprises a pipette, a manipulator for holding and moving said pipette up and down with respect to a predetermined position above said culture tray and a pump for drawing and discharging a predetermined quantity of a cell fluid into and from said pipette, said cell selecting section comprises a colony observatory section and an assay section, said assay section comprising and antibody detecting tray support for supporting thereon an antibody detecting tray provided with a plurality of walls therein, and a second drive means for grasping and transporting said antibody detecting tray onto said antibody detecting tray support, and a detector selected from group consisting of means for detecting the degree of color development by an enzyme antibody method or a means for defining spectra of liquid chromatography; and said controller comprises a device which generates and transmits at least five control signals for controlling each of said sections according to operating conditions of each of said sections inputted thereto, whereby said sections of said cell selecting apparatus operably interrelate and communicate in sequential steps including, (a) in response to a second signal, positioning said culture tray on said transport section tray support by said tray chuck, (b) in response to a first signal, moving said culture tray by said first drive means to said colony observatory section, and in response to a first measurement signal from said colony observatory section, measuring number and size of colonies, (c) in response to a third signal, moving said pipette to a position above a well provided in said culture tray, (d) in response to a fourth signal, extracting a cell supernatant from said well in said culture tray via said pump, (e) in further response to said third signal, moving said pipette containing said cell supernatant to a position above a well of said antibody detecting tray, (f) in further response to said fourth signal, injecting said cell supernatant from said pipette into said well of said antibody detecting tray, (g) in response to said first and second signals and a fifth signal, transporting said antibody detecting tray to said assay section by said second drive means, and (h) in response to a second measurement signal from said assay section, measuring the quantity of antibodies contained in said cell supernatant and storing this information in said controller, and calculating the antibody producing capability of the cells from this value.

4. The cell selecting apparatus as defined in claim 3 wherein said detector comprises:
an ELISA analyzer.

5. A cell selecting apparatus, comprising:
an extracting and injecting section;
a tray transport section for transporting at least one tray having a plurality of wells;
a cell selecting section; and
a controller,
wherein said extracting and injecting section comprises a pipette, a manipulator for holding and moving said pipette up and down at a predetermined position above a cell culture tray and a pump for drawing and discharging a predetermined quantity of a cell solution into and from said pipette,
said tray transport section comprises a tray support for supporting thereon a cell culture tray provided with a plurality of wells, a tray chuck and a first drive means for transporting said tray support to predetermined positions with respect to said extracting and injecting section and cell selecting section,
said cell selection section comprises a cell number counting section and a cell isolating section, said cell number counting section comprises a glass plate transport section and a second drive means for moving said glass plate from a position below said pipette at which said cell solution is dropped, to an observatory position for a microscope where said cell solution on said glass plate is observed, and a control circuit for counting the number of cells observed by the microscope through a TV camera,
said cell isolating section comprises a diluting vessel into which said cell solution extracted by said extracting and injecting section from wells of said cell culture tray having a predetermined number of cells specified by said cell number counting section through said controller is injected, and said cell isolating and said injecting section having a cell solution passage into which diluted cell solution is drawn from said diluting vessel, and a cell detecting section disposed in said passage, said tray transport section is operable in synchronism with a cell detection signal from a cell detecting section to move said cell culture tray a distance corresponding to the space between said wells at an outlet of said cell solution passage, and
said controller comprises a device which generates and transmits at least six controlling each said section according to operating conditions for each said section inputted thereto, whereby said sections of said cell selecting apparatus operably interrelate and communicate in sequential steps including,
(a) in response to a first signal, moving said pipette to a position above one of said wells of said cell culture tray via said manipulator of said extracting and injecting section,
(b) in response to a second signal, extracting said cell solution from said one of said wells of said cell culture tray,
(c) in further response to said first signal, positioning said pipette containing said cell solution above said glass plate of said cell number counting section,
(d) in further response to said second signal, injecting said cell solution contained in said pipette onto said glass plate of said cell number counting section,
(e) in response to a fifth signal, moving said glass plate to a position below the microscope, and in response to a first measurement signal from said cell number counting section, counting the number of cells viewable within a field of sight on said glass plate and calculating a concentration of cells in said cell solution,
(f) in further response to said first signal, returning said pipette to said cell culture tray,
(g) in further response to said second signal, extracting said cell solution from one of said wells of said cell culture tray,
(h) in further response to said first signal, moving said pipette to said diluting vessel via said manipulator of said extracting and injecting section,
(i) in further response to said second signal, injecting said cell solution into said diluting vessel,
(j) in response to a sixth signal, adding diluting liquid to said diluting vessel, and in response to a second measurement signal, detecting the passage of cells in said diluted cell solution past a detecting position,
(k) in further response to said third and fourth signals, moving a second culture tray of said tray transport system a distance of one of said wells of said cell culture tray at the outlet of said cell solution passage.

6. The cell selecting apparatus as defined in claim 5 wherein said cell detecting section comprises:
a pair of electrodes on respective sides of said cell solution passage.

7. The cell selecting apparatus as defined in claim 5 wherein said cell detecting section comprises:
a light emitter and a light receiver positioned on respective sides of said cell solution passage.

8. A cell selecting apparatus, comprising:
an extracting and injecting section;
a tray transport section for transporting at least one cell culture tray;
a controller; and
a cell selecting section,
wherein said extracting and injecting section comprises a pipette, manipulator for holding the pipette and for moving the pipette up and down at a predetermined position above said culture tray and a pump for drawing and discharging a predetermined quantity of a cell solution into and from said pipette,
said tray transport section comprises a transport section tray support for supporting thereon one said cell culture tray provided with a plurality of wells therein, a first tray chuck and a first drive means for transporting one said cell culture tray to predetermined positions with respect to said extracting and injecting section and said cell selecting section,
said cell selecting section comprises a cultivating section, a colony observation section, an assay section, a cell number counting section and a cell isolating section,
wherein said cultivating section comprises an incubator including a tray stock for accommodating a pluralilty of said cell culture trays, a second tray chuck and a second drive means for moving said tray stock and a cultivating section tray support for transporting said cell culture trays to said tray stock, and further said cultivating section being operable to interact with said extracting and injecting section in a manner such that said pipette can be manipulated to a predetermined position at which location said cell solution may be injected into or extracted from a cell colony without disturbing the growth of said colony, said assay section comprises an antibody detecting tray support for supporting thereon an antibody detecting tray provided with a plurality of wells therein, and said second drive means for grasping and transporting said antibody detecting tray onto said antibody detecting tray support, and a detector selected from the group consisting of means for detecting the degree of color development by an enzyme antibody method or a means for defining spectra of liquid chromatography, said cell number counting section comprises a glass plate transport section and a third drive means for moving said glass plate from a position below said pipette at which said cell solution is dropped, to an observatory position for a microscope where said cell solution on said glass plate is observed, and a control circuit for counting the number of cells observed by the microscope through a TV camera, said cell isolating section comprises a diluting vessel into which said cell solution extracted by said extracting and injecting section from wells of said cell culture tray in which said cells secrete antibodies, and said cell isolating section having a cell solution passage into which diluted cell solution is drawn from said diluting vessel and a cell detecting section disposed in said passage, and said tray transport section is operable in synchronism with a cell detecting signal from said cell detecting section to move said cell culture tray a distance corresponding to the space between said wells at an outlet of said cell solution passage, and said controller comprises a device which generates and transmits control signals for controlling each said section according to operating conditions for each said inputted thereto, whereby said section of said cell selecting apparatus operably interrelate and communicate in sequential steps including, (a) in response to a first measurement from said colony observatory section, measuring number and size of colonies, and replacing the supernatant of the cell culture tray to fresh liquid culture or drawing said supernatant of said cell solution to detect the quantity of antibody, (b) in response to a second measurement signal from said assay section, measuring the quantity of antibody of said wells of the cell culture tray and detecting the well producing the greater quantity of antibody, and drawing the cell solution of the well to measure the cell number of the cell solution, (c) in response to a third measurement signal from said cell number counting section, measuring the cell number and determining the degree of dilution with respect to a predetermined concentration, and diluting the cell solution to isolate the cells.

* * * * *